US008252902B2

(12) United States Patent
Barbas et al.

(10) Patent No.: US 8,252,902 B2
(45) Date of Patent: Aug. 28, 2012

(54) ANTIBODY TARGETING COMPOUNDS

(75) Inventors: Carlos F. Barbas, Solana Beach, CA (US); Christoph Rader, San Diego, CA (US); Subhash C. Sinha, San Diego, CA (US); Richard A. Lerner, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 2085 days.

(21) Appl. No.: 10/278,364

(22) Filed: Oct. 22, 2002

(65) Prior Publication Data

US 2003/0175921 A1 Sep. 18, 2003

Related U.S. Application Data

(60) Provisional application No. 60/344,614, filed on Oct. 22, 2001, provisional application No. 60/412,455, filed on Sep. 19, 2002.

(51) Int. Cl.
C07K 16/00 (2006.01)
(52) U.S. Cl. ............... 530/387.1; 424/9.34; 424/130.1; 424/178.1; 424/179.1
(58) Field of Classification Search .................. None
See application file for complete search history.

(56) References Cited

U.S. PATENT DOCUMENTS

| | | | |
|---|---|---|---|
| 4,722,892 A | 2/1988 | Meares et al. | |
| 5,055,289 A | 10/1991 | Frincke et al. | |
| 5,162,218 A | 11/1992 | Schultz | |
| 5,302,516 A | 4/1994 | Schultz | |
| 5,693,636 A | 12/1997 | Bondinell et al. | |
| 6,001,117 A | 12/1999 | Huxel et al. | |
| 6,008,321 A | 12/1999 | Li et al. | |
| 6,040,311 A | 3/2000 | Duggan et al. | |
| 6,045,774 A | 4/2000 | Hiatt et al. | |
| 6,096,725 A | 8/2000 | Simon et al. | |
| 6,238,667 B1 | 5/2001 | Kohler | |
| 6,251,392 B1 * | 6/2001 | Hein et al. | 424/134.1 |
| 6,265,540 B1 | 7/2001 | Isaacs et al. | |
| 6,268,488 B1 * | 7/2001 | Barbas et al. | 536/6.4 |
| 6,335,330 B1 | 1/2002 | Ross | |
| 6,391,280 B1 | 5/2002 | Hiatt et al. | |
| 6,440,419 B1 | 8/2002 | Hein et al. | |
| 7,521,425 B2 * | 4/2009 | Bradshaw et al. | 514/1.1 |

FOREIGN PATENT DOCUMENTS

| | | |
|---|---|---|
| EP | 0217577 | 10/1992 |
| EP | 0 510 949 B1 | 1/1997 |
| WO | WO 97/37690 | 10/1997 |
| WO | WO 98/22141 | 5/1998 |
| WO | WO 98/25895 | 6/1998 |
| WO | WO 99/15178 | 4/1999 |
| WO | WO 01/10867 | 2/2001 |
| WO | WO 01/22922 | 4/2001 |
| WO | WO 02/36073 A2 | 5/2002 |

OTHER PUBLICATIONS

Rader et al. 'A Humanized Aldolase Antibody for Select,Chemotherapy and Adaptor Immunotherapy.' J. Mol. Biol. (2003), vol. 332, pp. 889-899.*
Li et al. 'Chemical Adaptor Immunotherapy: Design, Synthesis, and Evaluation of Novel Integrin Targeting Devices.' J. Med. Chem. vol. 2004, No. 47, pp. 5630-5640.*
Tanaka et al. 'Thiazolium-dependent catalyctic antiboides produced using a covalent modification strategy.' Chem. Commun. 1999, pp. 1383-1384.*
Kok, et al., "Preparation and Functional Evaluation of RGD-Modified Proteins as $\alpha_v\beta_3$ Integrin Directed Therapeutics", *Bioconjugate Chem.* 13: 128-135 (2002).
Gopalakrishnan, "Affinity Labeling of Anti-Lactose Antibodies with Bromoacetylaminolac Dye in Dark", *Immunol. Commun.* 4: 499-506 (1975).
Gopalakrishnan, et al., "Affinity-Labeling of Anti-Lactose Antibody", *Immunochemistry* 12: 449-452 (1975).
Gopalakrishnan, et al., "Labeling of Antilactose Antibody", *Methods Enzym. XLVI*: 516-523 (1977).
Endo, et al., "A Novel Covalent Modification of Antibodies at Their Amino Groups with Retention of Antigen-binding Activity", *J. Immunol. Methods* 104: 253-258 (1987).
Shokat, et al., "Redirecting the Immune Response: Ligand-Mediated Immunogenicity", *J. Am. Chem. Soc.* 113: 1861-1862 (1991).
Canevari, et al., "Immunoconjugates: Lessons from Animal Models", *Ann. Oncol.* 5: 698-701 (1994).
Janda, et al., "Direct Selection for a Catalytic Mechanism from Combinatorial Antibody Libraries", *Proc. Natl. Acad. Sci. USA* 91: 2532-2536 (1994).
Lussow, et al., "Targeting of Activated T-Cells with Natural Cytotoxic Antibodies via an IL2-Hapten Conjugate Prolongs Graft Survival", *Transplant. Proceedings* 28: 571-572 (1996).
Lussow, et al., "Redirecting Circulating Antibodies via Ligand-Hapten Conjugates Eliminates Target Cells In Vivo", *J. Immunotherapy* 19: 257-265 (1996). Lussow, et al., "Targeting of Antihapten Antibodies to Activated T Cells via an IL-2-Hapten Conjugate Prolongs Cardiac Graft Survival", *Transplantation* 62: 1703-1708 (1996).
Debnath, et al., "Structure-Based Identification of Small Molecule Antiviral Compounds Targeted to the gp4I Core Structure of the Human Immunodeficiency Virus Type 1", *J. Med. Chem.* 42: 3203-3209 (1999).
Tanaka, et al., "Catalytic single-chain antibodies possessing $\beta$-lactamase activity selected from a phage displayed combinatorial library using a mechanism-based inhibitor", *Tetrahedron Lett.* 40: 8063-8066 (1999).
Shabat, et al., "Multiple event activation of a generic prodrug trigger by antibody catalysis", *Proc. Natl. Acad. Sci. USA* 96: 6925-6930 (1999).

(Continued)

*Primary Examiner* — Anish Gupta
(74) *Attorney, Agent, or Firm* — Hugh Wang; Thomas Fitting; Andrew Serafini

(57) ABSTRACT

The present invention provides antibody targeting compounds in which the specificity of the antibody has been reprogrammed by covalently or noncovalently linking a targeting agent to the combining site of an antibody. By this approach, the covalently modified antibody takes on the binding specificity of the targeting agent. The compound may have biological activity provided by the targeting agent or by a separate biological agent. Various uses of the invention compounds are provided.

28 Claims, 15 Drawing Sheets

OTHER PUBLICATIONS

Kiaris, et al., "A targeted cytotoxic somatostatin (SST) analogue, AN-238, inhibits the growth of H-69 small-cell lung carcinoma (SCLC) and H-157 non-SCLC in nude mice", *Eur. J. Cancer 37*: 620-628 (2001).

Adlington, et al., "Design, Synthesis, and Proposed Active Site Binding Analysis of Monocyclic 2-Azetidinone Inhibitors of Prostate Specific Antigen", *J. Med. Chem. 44*: 1491-1508 (2001).

Shabat, et al., "In vivo activity in a catalytic antibody-prodrug system: Antibody catalyzed etoposide prodrug activation for selective chemotherapy", *Proc. Natl. Acad. Sci. USA 98*: 7528-7533 (2001).

Chmura, et al., "Antibodies with infinite affinity", *Proc. Natl. Acad. Sci. USA 98*: 8480-8484 (2001).

Lian, et al., "Preparation and Properties of a Selenium-containing Catalytic Antibody as Type I Deiodinase Mimic", *J. Biol. Chem. 276*: 28037-28041 (2001).

Nicholas, et al., "A Cofactor Approach to Copper-Dependent Catalytic Antibodies", *Proc. Natl. Acad. Sci. USA 99*: 2648-2653 (2002).

Lu, et al., "Folate Targeting of Haptens to Cancer Cell Surfaces Mediates Immunotherapy of Syngeneic Murine Tumors", *Cancer Immunol. Immunother. 51*: 153-162 (2002).

U.S. Appl. No. 09/822,379, filed Oct. 18, 2001, Low, P. S.; Lu, Y.

U.S. Appl. No. 09/921,663, filed Jan. 24, 2002, Pouletty, P.; Pouletty, C.

Wagner, et al., "Efficient Aldolase Catalytic Antibodies That Use the Enamine Mechanism of Natural Enzymes", *Science 270*: 1797-1800 (1995).

Popkov, et al., "Small molecule drug activity in melanoma models may be dramatically enhanced with an antibody effector", *Int. J. Cancer 119*: 1194-1207 (2006).

Wuellner, et al., "Expanding the Concept of Chemically Programmable Antibodies to RNA Aptamers: Chemically Programmed Biotherapeutics", *Angew. Chem. Int. Ed. 49*: 1-5 (2010).

\* cited by examiner

Figure 1
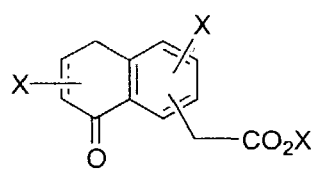
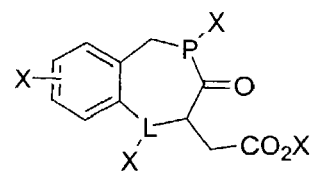
A
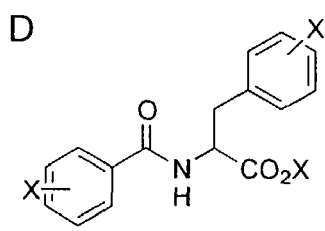
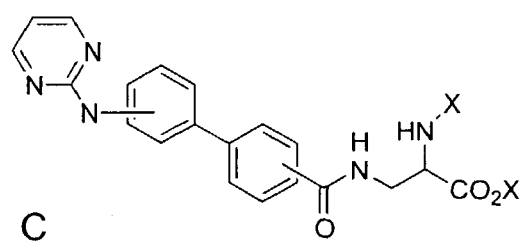
B
C
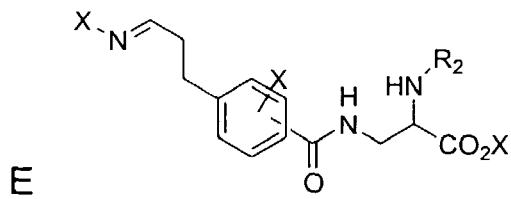
D
E
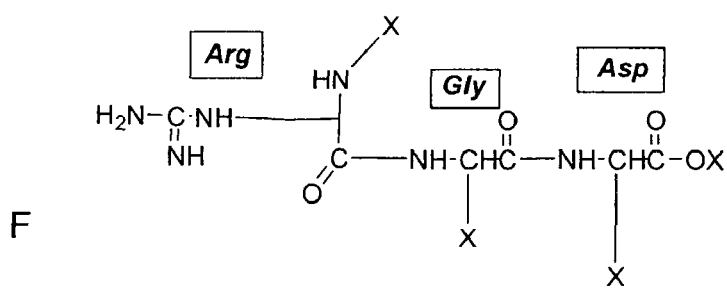
F Figure 2
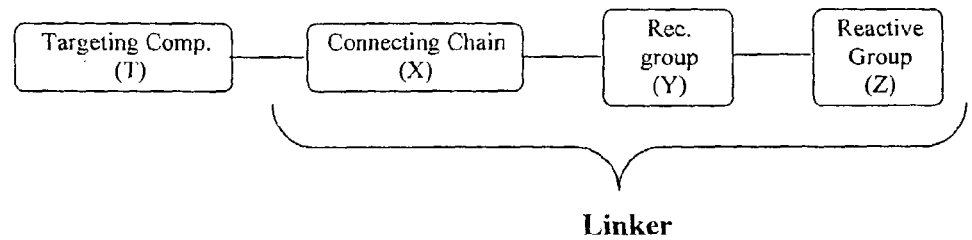
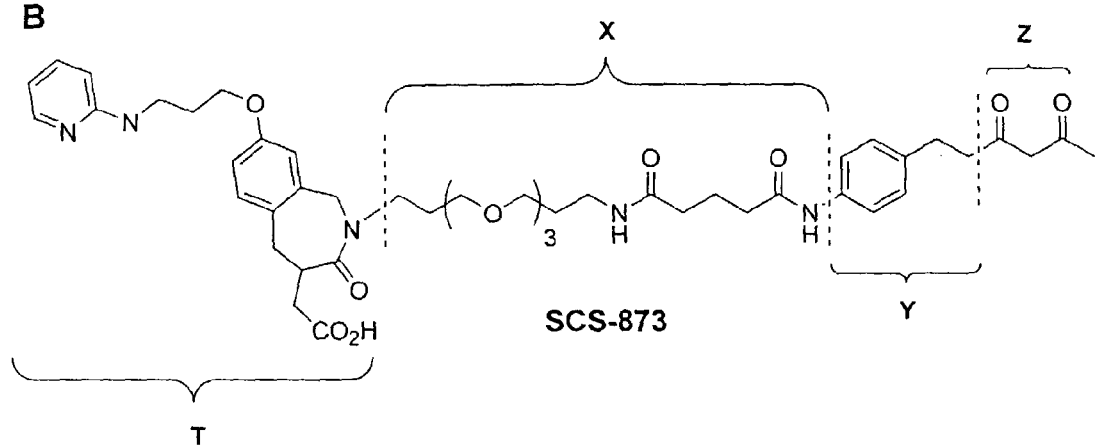
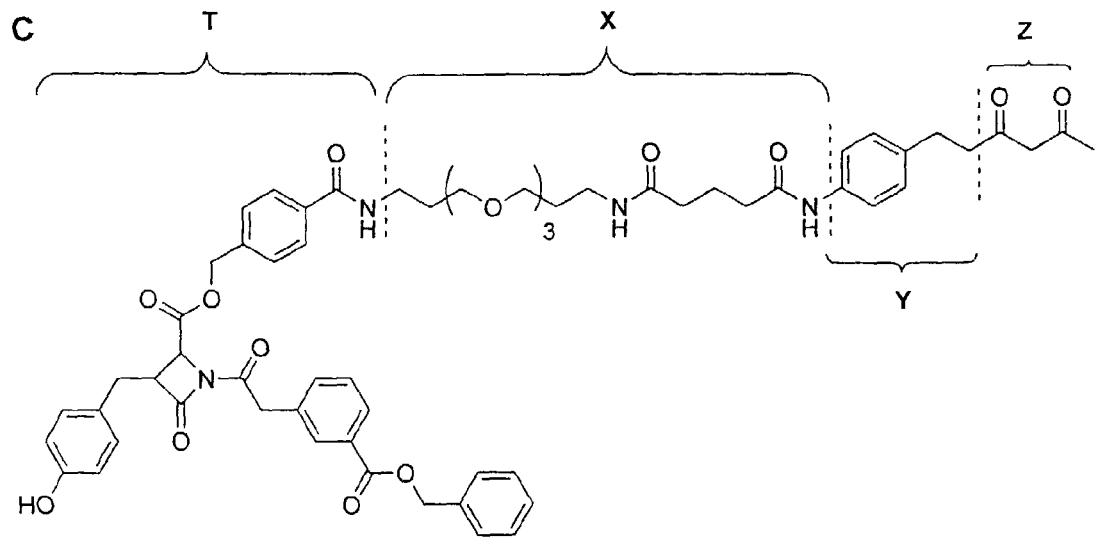

Figure 3
A
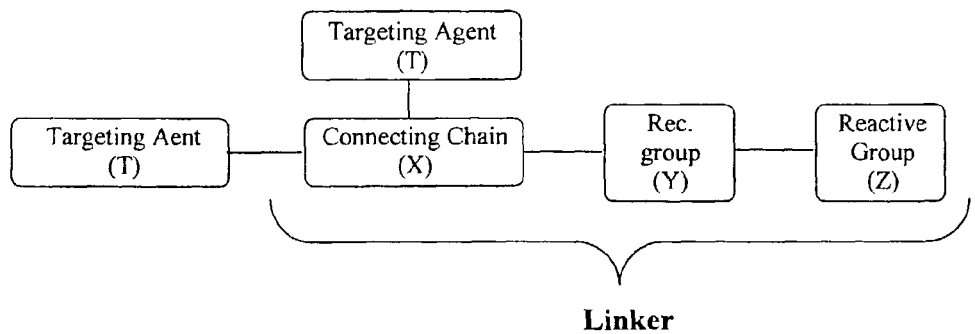
B
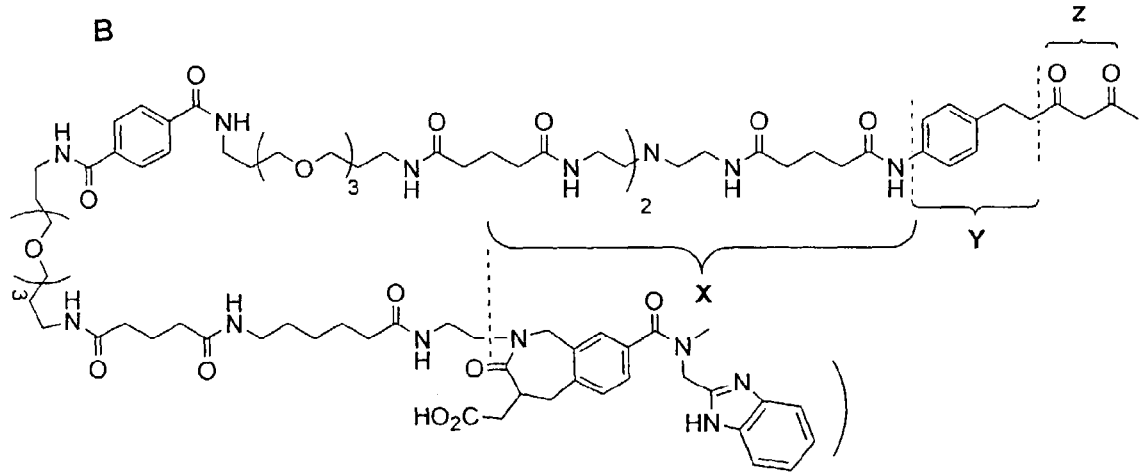
C
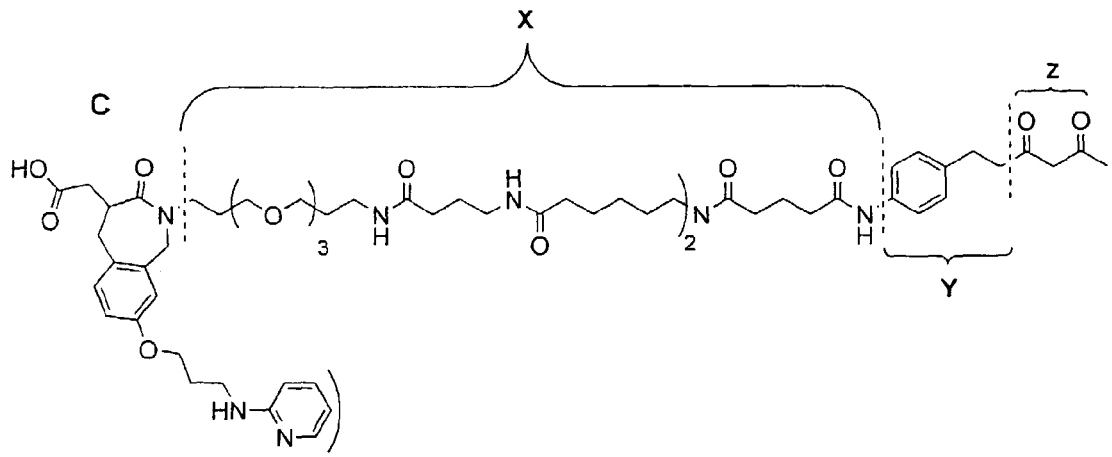

Figure 4
A
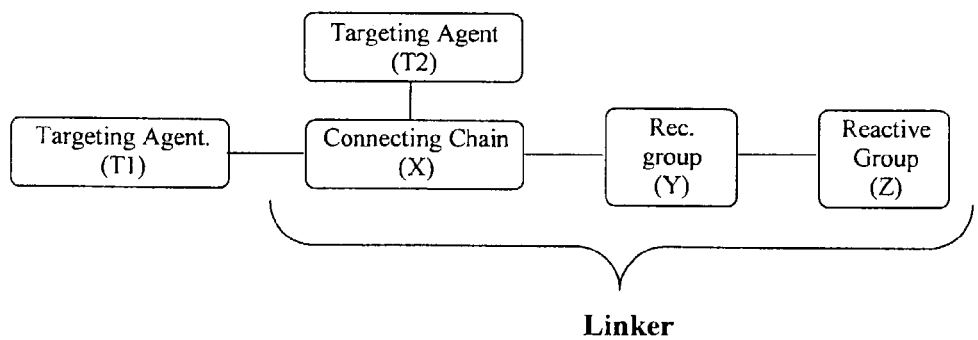
B
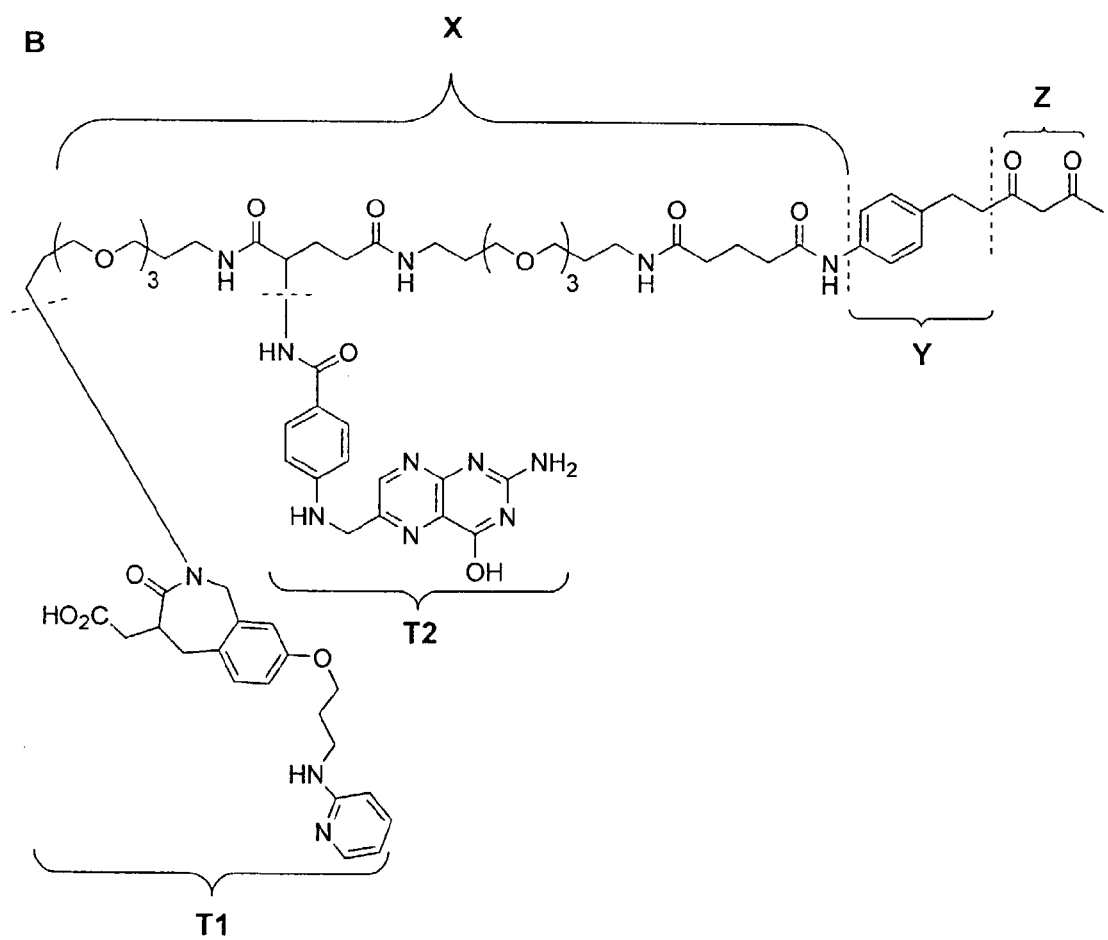

Figure 5
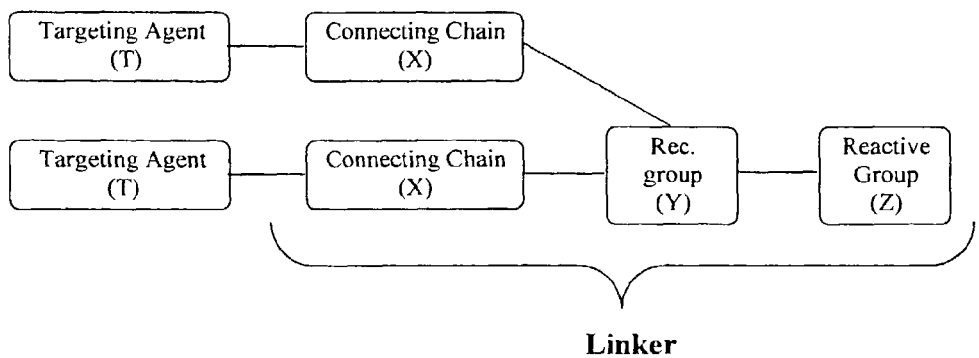
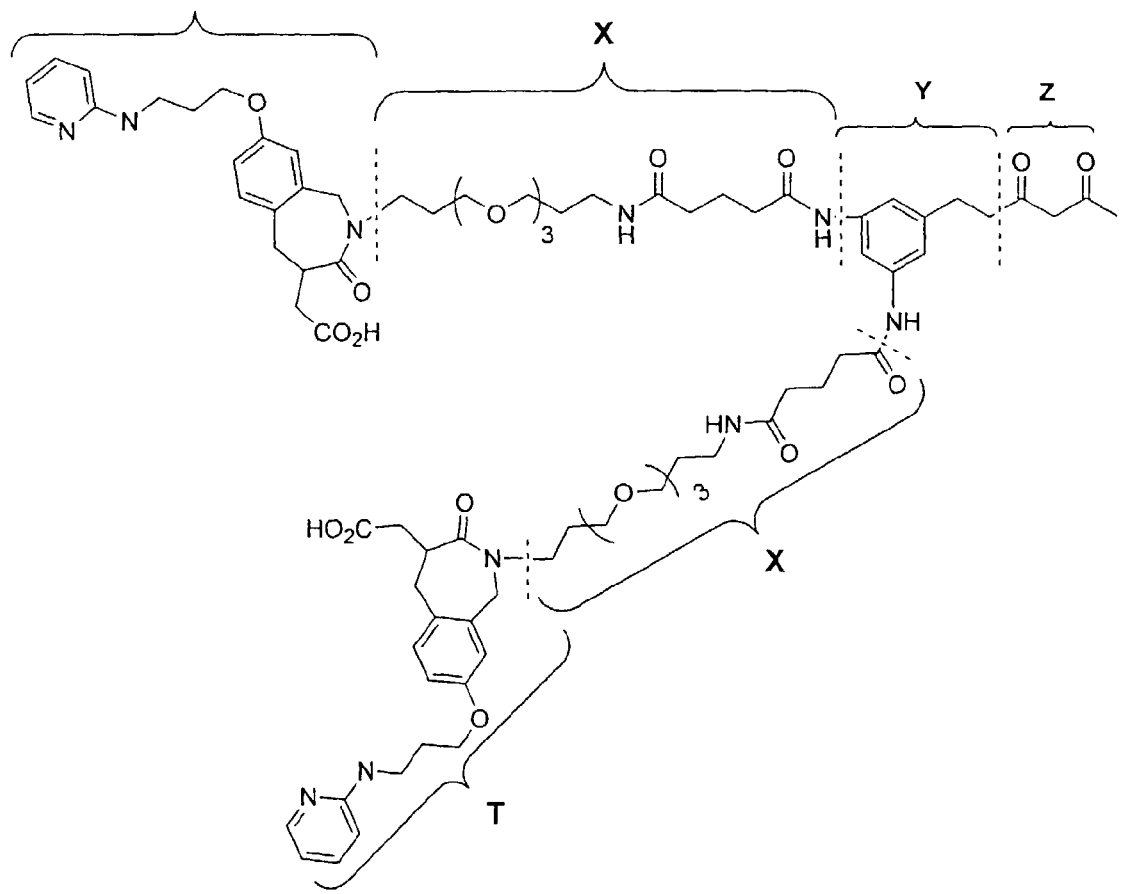

Figure 6
Linker Reactive Groups (Z)
A
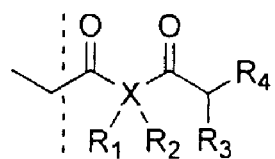
B
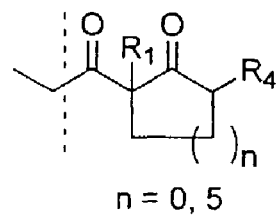
n = 0, 5
C
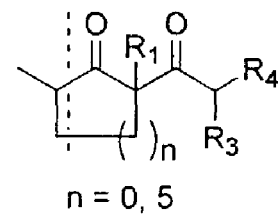
n = 0, 5
D
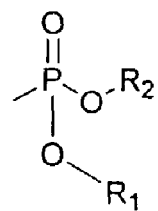
E
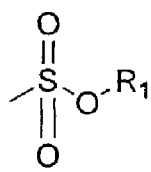
F
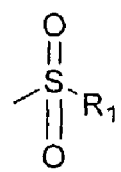
G
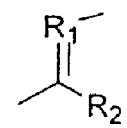

Figure 7
A
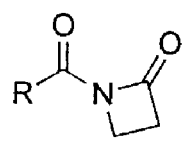
B
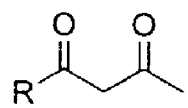
C
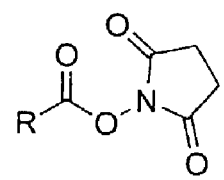
D
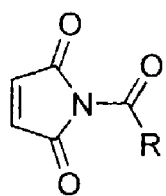
E
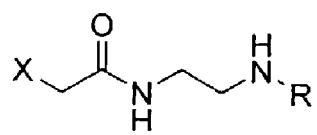
F
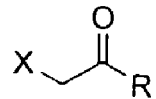
G
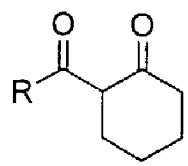
H
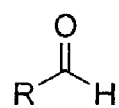

Figure 8
Linker Recognition Groups (Y)
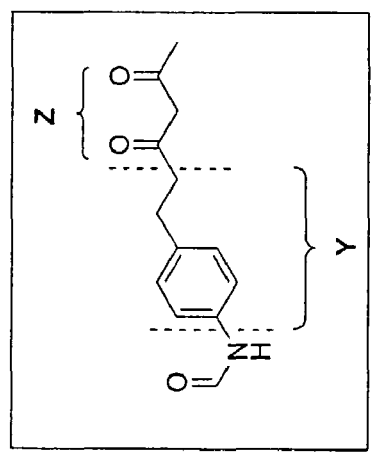
A
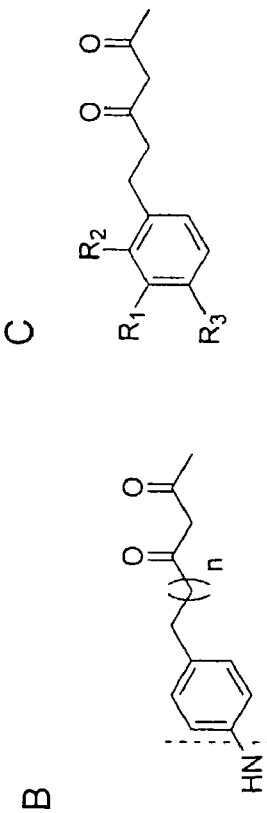
B
n = 1-5
C
R1, R2, R3 = O-R, S-R, N-R, CH2-R
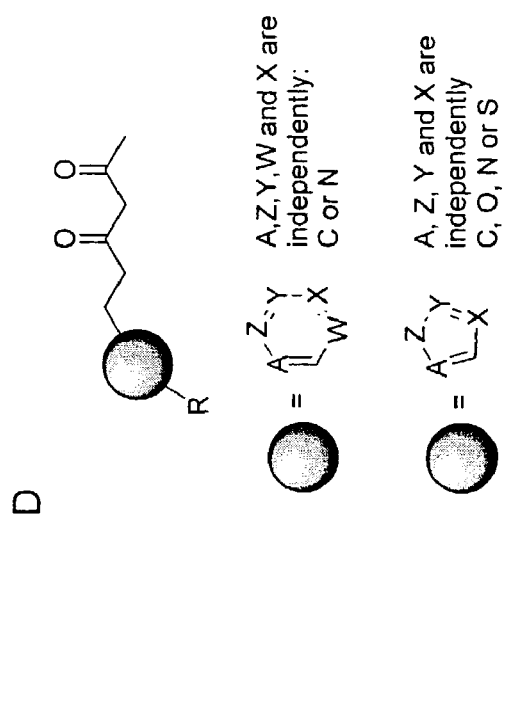
D
A, Z, Y, W and X are independently: C or N
A, Z, Y and X are independently C, O, N or S Figure 9
Linker Connecting Chain (X)
A
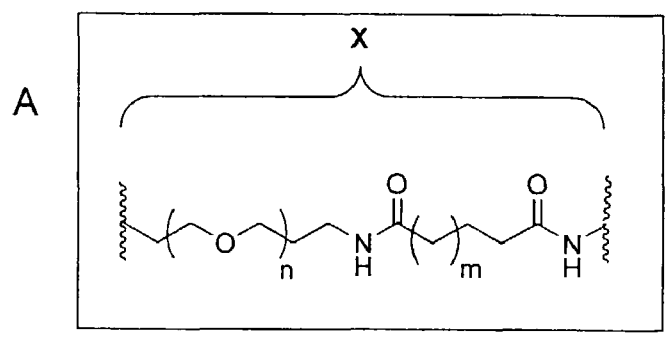
B
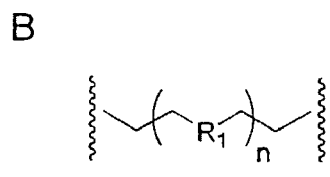
R1 = O, CH2, NR1R2,
Si, S, S(O), S(O)2
D
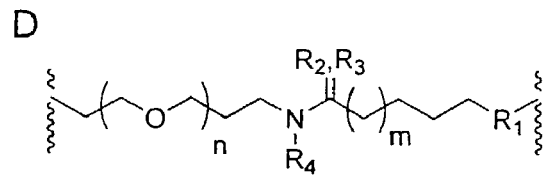
C
Branched Chain:
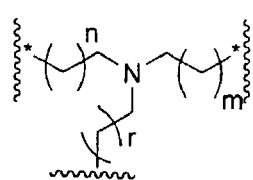
E
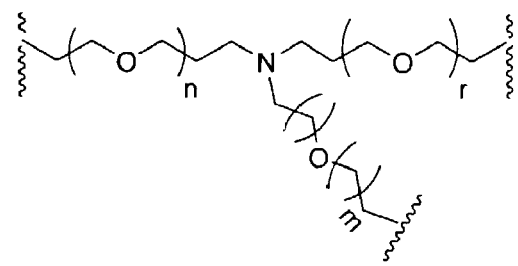

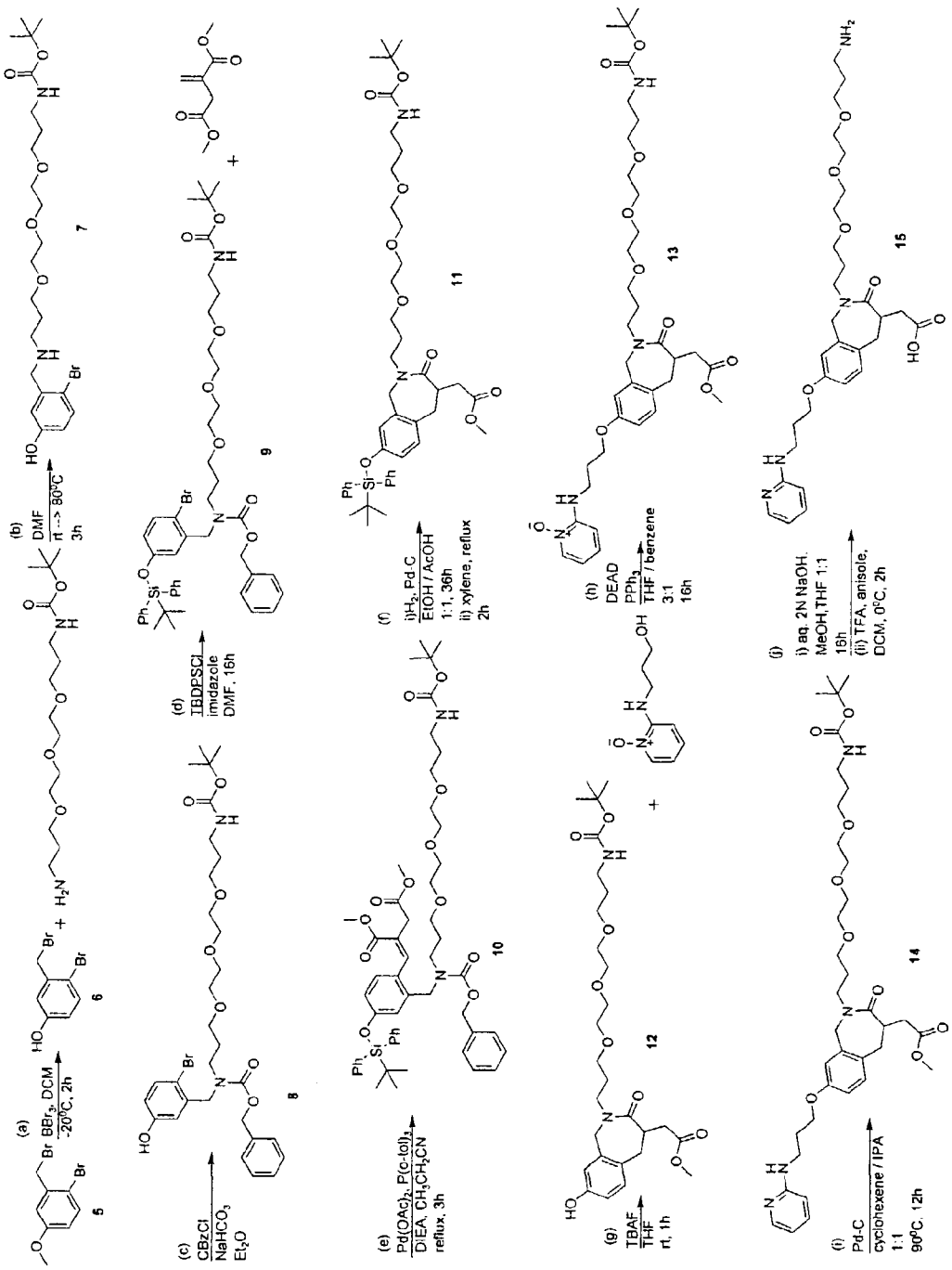
FIG. 10 (Scheme 1)

FIG. 11 (Scheme 2)
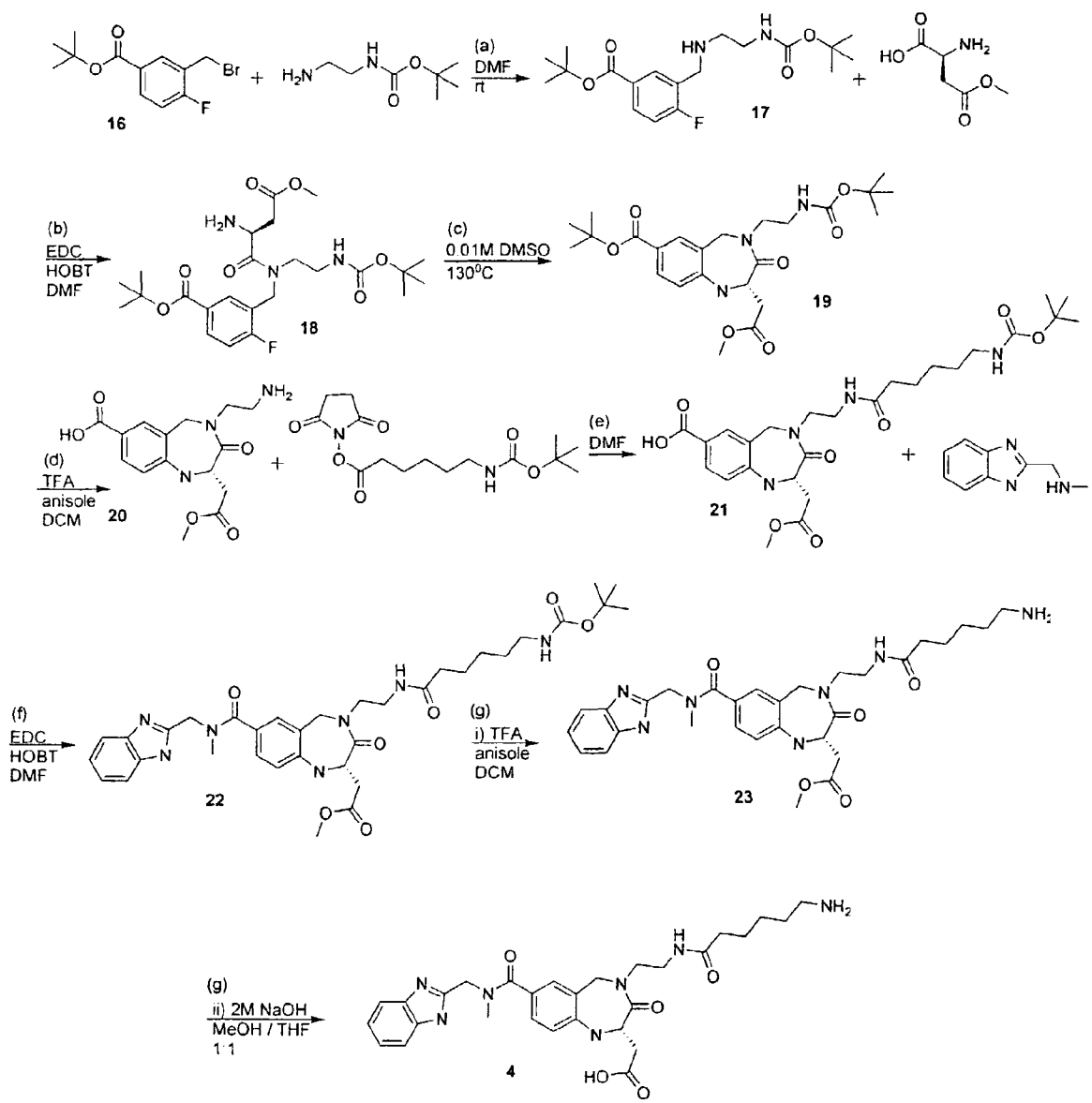

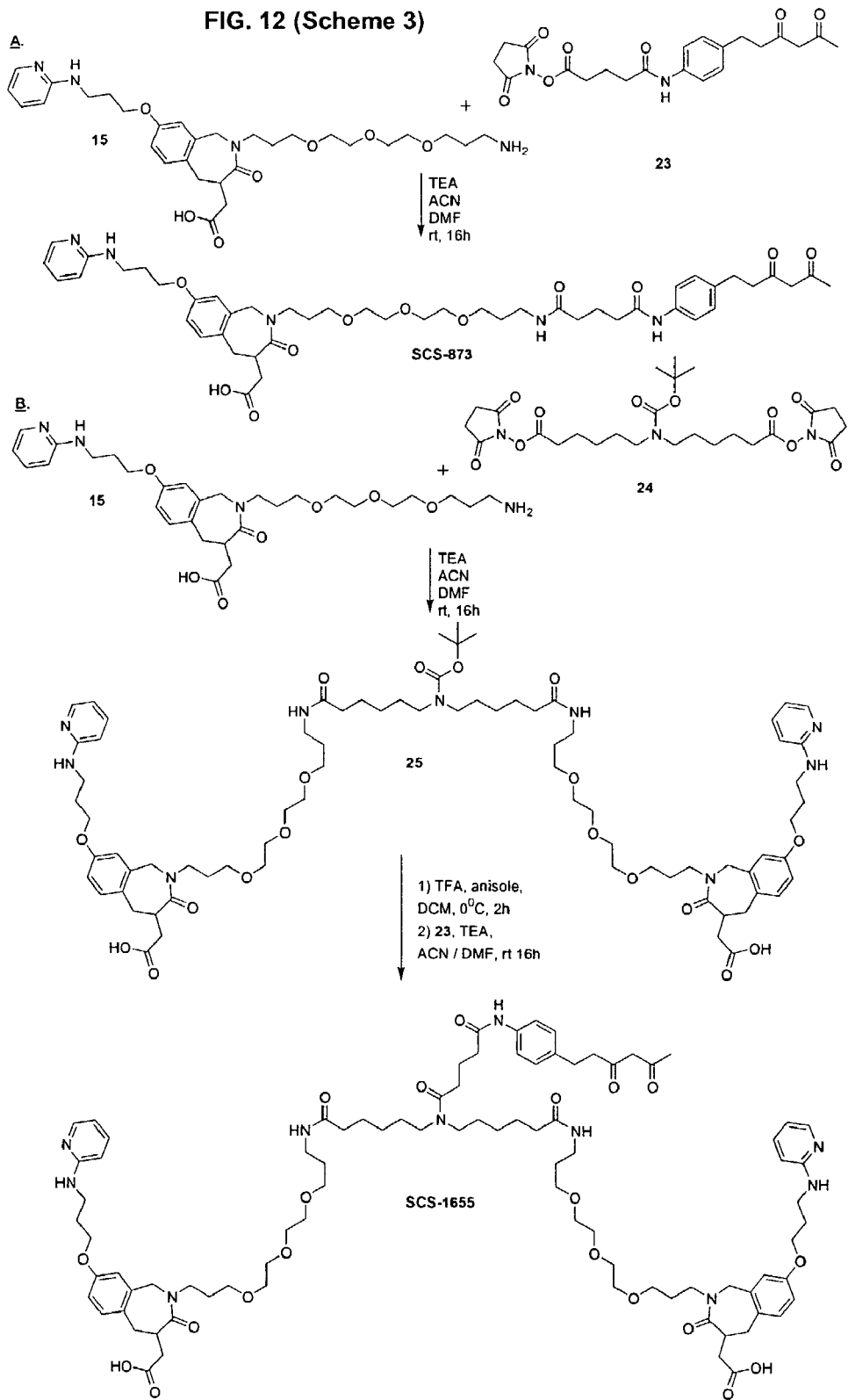
FIG. 12 (Scheme 3)

FIG. 13 (Scheme 4)
Reaction A
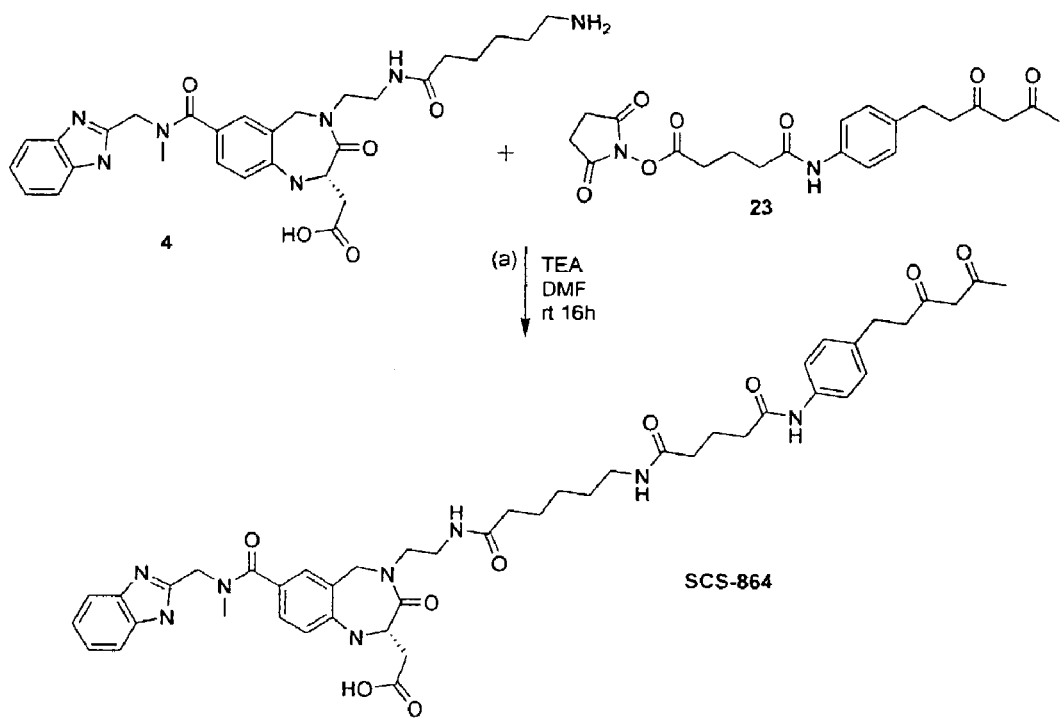
Reaction B
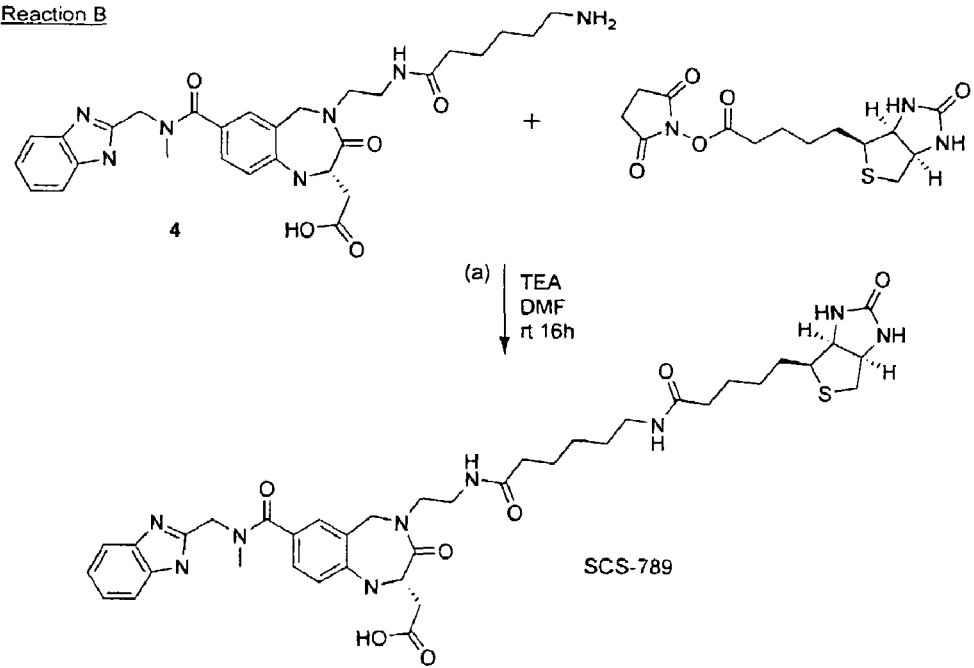

ANTIBODY TARGETING COMPOUNDS

This invention was made with United States Government support under Grant Nos. CA27489 and CA86258 by the National Institutes of Health. The United States Government has certain rights in the invention.

BACKGROUND OF THE INVENTION

The invention relates to compounds for targeting biological molecules and methods of making and using the compounds. Conventionally developed pharmaceutical drugs and biological effector molecules are often of limited use in therapy because of high toxicity. Various approaches have been used over the years to improve the therapeutic index of such drugs or effectors. One approach has been to couple a drug or effector to a ligand targeting agent such as an antibody. In this case, the antibody is used to change the distribution of drug or effector such that more of it can localize where it is most needed in vivo. Improved targeting of small molecular weight drugs or effectors has been achieved by complexing the drug or effector with a large molecular weight compound. For example, European Patent EP 217577 discloses that increased half life and targeting by an agent is achieved by forming complexes in vivo between hapten-modified agents and anti-hapten antibodies. Similarly, International Patent Application Publication WO 98/22141 discloses conjugates of therapeutic agents and haptens. The conjugates are administered to a subject and circulate in the blood stream of the subject. Circulating conjugates are recognized and bound by existing antibodies in the subject. Also, Shokat and Schultz (J. Am. Chem. Soc., 1991, 113:1862-1864) have disclosed a process for redirecting the immune response using a process referred to as ligand-mediated immunogenicity. According to this teaching, an invariant antigen is complexed with a specific ligand and administered to a subject. The complexed invariant antigen then binds naturally occurring antibodies present in the subject.

BRIEF SUMMARY OF THE INVENTION

The present invention provides antibody targeting compounds with unique specificity and biological properties which are useful in many applications. The antibody targeting compounds of the invention comprise one or more targeting agents or biological agents or both covalently or noncovalently linked to an antibody combining site. A linear or branched linker is preferably used in covalent and non-covalent linkage. Chemical characteristics of the linker are disclosed. Depending on the circumstances, the antibody specificity of the combining site may be modified or eliminated following covalent or noncovalent linking to the targeting or biological agent. In some embodiments, the antigen binding specificity of the antibody before covalent linkage may be substantially retained after covalent linkage.

The antibody targeting compound confers various benefits over the components themselves. For example, the antibody portion of the compound may generally extend the half-life of a smaller sized targeting or biological agent in vivo. Also, the biological potency or other biological feature of a particular targeting or biological agent may be modified by the addition of effector function(s) provided by the antibody portion of the compound (e.g., complement mediated effector functions). In addition, the targeting agent or binding agent, through its increased size conferred by linkage to the antibody, may enable the targeting agent to function in new capacities.

In some embodiments, the targeting agent of the compound can bind to a non-immunoglobulin target molecule or to an immunoglobulin target molecule outside of the immunoglobulin combining site. Thus, in these embodiments, the targeting agent is specific for a non-antibody or is specific for an antibody but binds to the antibody outside its combining site. In a preferred approach, a catalytic antibody can be modified into a compound that binds specifically to a biomolecule. The antibody portion of the antibody targeting compounds can include whole antibody or unique antibody fragments and may have sequence derived from various animal species such as a non-human immunoglobulin or human immunoglobulin, the latter including a human antibody, humanized antibody or human chimeric antibody.

Also provided are methods of producing antibody targeting compounds of the invention. In one embodiment, an agent-linker compound comprising a targeting agent and/or a biological agent is linked to a linker that comprises a reactive group for covalent reaction with the combining site of the antibody. In another approach, an antibody-linker compound is prepared where the linker includes a reactive group for reaction with said one or more targeting agents or biological agents. In yet another approach, the agents and the antibody can each be linked to a linkers with compatible reactive groups so that the antibody targeting compound forms when the two linkers covalently bond.

Further provided are agent-linker compounds comprising a targeting agent, biological agent or both that can be covalently linked to the combining site of an antibody. In some embodiments, the linker includes a reactive group for covalently linking the targeting agent to the combining site of the antibody. Linkage to the antibody combining site may be to a side chain of a reactive amino acid in the combining site. In some embodiments, the reactive amino acid is a lysine while the linker reactive group is a ketone, a diketone, a beta lactam, a succinimide active ester, haloketone, a lactone, an anhydride, an epoxide, an aldehyde, a halide, a sulfonate, a phosphonate, a guanidine, an amidine, an imine, an eneamine, a ketal, a acetal, or a maleimide.

Various chemical features of the agent-linker compound are described. In one embodiment, the linker has the general formula X—Y—Z wherein X is a linear or branched connecting chain of atoms comprising any of C, H, N, O, P, S, Si, F, Cl, Br, and I, or a salt thereof, and comprising a repeating ether unit of between 2-100 units; Y is optional and is a single or fused 5 or 6 membered homo- or heterocarbocylic saturated or unsaturated ring located within 1-20 atoms of Z; and Z is a reactive group for covalently linking the one or more targeting agents to a side chain of a reactive amino acid in the combining site of the antibody. The targeting agent may be linked to X or Y or to X and Y when more than one targeting agent or biological agent is included in the targeting agent-linker compound.

Yet further provided are targeting agent-linker-antigen compounds for noncovalently linking to the combining site of an antibody. These compounds include two or more targeting agents, two or more biological agents or at least two agents, one of which is a targeting agent and another a biological agent. The agents are covalently linked via a linker to an antigen recognized by the antibody. Various chemical features of the linker and antigen are disclosed.

Still further provided are methods of modifying an antibody which exhibits low or nondetectable binding affinity for a particular target molecule so that the antibody has increased binding specificity for the particular target molecule. In one embodiment, one or more targeting agents or biological agents specific for the particular target molecule are covalently linked to the combining site of the antibody to generate an antibody targeting compound. The agents are linked in such a way as to retain their ability to bind the particular target molecule. In some such embodiments, the antibody prior to covalent linking possesses an affinity for the target molecule of less than about $1\times10^{-5}$ moles/liter. After covalent linking, the targeting compound may exhibit an affinity for the target molecule of greater than about $1\times10^{-6}$ moles/liter.

Additionally provided are methods of altering at least one physical or biological characteristic of a targeting agent or biological agent. In one embodiment, the agent is covalently linked to the combining site of an antibody to generate an antibody targeting compound. Methods are also provided for modifying one or more physical or biological properties of the antibody targeting compounds by modifying one or more chemical characteristics of the linker. In some embodiments, the physical or biological properties modified include pharmacokinetics, pharmacodynamics, immunogenicity, binding affinity, susceptibility to degradation, solubility, lipophilicity, hydrophilicity, hydrophobicity, stability, and rigidity.

Also provided are methods of delivering a biological activity to cells, an extracellular matrix biomolecule or a fluid biomolecule of an individual. In one approach an antigen targeting compound of the invention which is biologically active and is specific for the cells, extracellular matrix biomolecule or fluid biomolecule is administered to the individual. In another approach, an agent-linker-antigen compound of the invention, specific for cells, tissue extracellular matrix biomolecule or fluid biomolecule, and an antibody specific for the antigen are separately administered to the individual and the antibody targeting agent forms in vivo when the agent-linker-antigen compound non-covalently associates with the antibody combining site.

Further provided are methods treating or preventing a disease or condition in an individual wherein the disease or condition involves cells, tissue or fluid that expresses a target molecule. In one approach, a therapeutically effective amount of an antibody targeting compound of the invention is administered to the individual. In another approach, a therapeutically effective amount of an agent-linker-antigen compound of the invention, and an antibody specific for the antigen are separately administered to the individual and the antibody targeting agent forms in vivo when the agent-linker-antigen compound non-covalently associates with the antibody combining site. In both approaches, the antibody targeting compound or agent-linker-antigen compound is specific for the target molecule, and the compound or antibody comprises a biological activity effective against the disease or condition.

Still further provided are methods of imaging cells or extracellular matrix in an individual wherein the cells or extracellular matrix express a target molecule. In one approach, an antibody targeting compound of the invention is linked to a detectable label and administered to the individual. In another approach an agent-linker-antigen compound and an antibody specific for the antigen are separately administered to the individual and the antibody targeting agent forms in vivo when the agent-linker-antigen compound non-covalently associates with the antibody combining site. In both approaches, the label may be linked to the antibody, the targeting agent and/or biological agent.

Additionally provided are methods of reducing the infectivity of microbial cells or viral particles present on a surface. According to these methods, the surface is contacted with an effective amount of an antibody targeting compound of the invention, wherein the antibody targeting compound comprises a targeting agent or biological agent specific for a receptor on said microbial cells or virus particles.

Also provided are methods of screening a chemical library for agonists or antagonists of a receptor. The method includes linking individual members of the chemical library to the combining site of an antibody and then testing the antibody linked library for binding to the receptor or for inhibition of binding between the receptor and a ligand for the receptor.

Further provided are various immunoassays that use antibody targeting compounds of the invention. In one embodiment for detecting or measuring analyte in a sample, the invention comprises use of an antibody targeting compound of the invention wherein the antibody specificity for the analyte results from the targeting agent, which is covalently linked to the antibody combining site. In another embodiment involving a direct or indirect binding assay for determining the presence of an analyte using an antibody specific for the analyte, the invention comprises determining the presence of the analyte using an antibody specific for the analyte wherein the antibody specificity results from a non-antibody targeting agent specific for the analyte that is linked to a reactive amino acid in the combining site of the antibody.

Still further provided are methods of inhibiting or reducing the ability of a targeting agent or biological agent to cross a cell membrane. In these methods an antibody targeting compound is formed by covalently linking the combining site of an antibody that does not itself cross the cell membrane to the targeting agent or biological agent, wherein linkage of said antibody to said targeting agent or biological agent reduces or inhibits the ability of the agent to cross the cell membrane.

Additionally provided are methods of mediating intracellular delivery of a intracellularly active drug. In these methods, an antibody targeting compound is prepared wherein said compound includes one or more targeting agents or one or more biological agents or both covalently linked via a linker to the combining site of the antibody. The targeting agents or biological agents are characterized in that they bind to a cell receptor and mediate internalization of the agent. The antibody targeting compound also includes a drug that is active intracellularly. Intracellular drug delivery occurs when a cell expressing the receptor contacts the antibody targeting compound. The contacting results in internalization of the antibody targeting agent and delivery of said drug intracellularly. In some embodiments, the intracellularly active drug is a prodrug that becomes active when said drug contacts an intracellular compartment. The antibody targeting compound may include an intracellular trafficking signal to direct the internalized antibody targeting compound to a particular intracellular compartment.

The invention further provides pharmaceutical compositions or medicaments that include an antibody targeting compound of the invention and a pharmaceutically acceptable carrier.

BRIEF DESCRIPTION OF THE DRAWINGS

FIG. 1 shows exemplary integrin targeting agents of which Panels A-E are RGD peptidomimetic while Panel F is an RGD peptide. The core structures are from the following: U.S. Pat. No. 6,335,330 (Panel A), U.S. Pat. No. 5,693,636 (Panel B), U.S. Pat. No. 6,040,311 (Panel C), and U.S. Pat. No. 6,001,117 (Panel E).

FIG. 3 shows a general scheme of an embodiment of a targeting agent-linker compound with a branched linker and two identical targeting agents (Panel A) with specific embodiments in Panel B (integrin targeting agent diketo linker; compound 29), and Panel C (integrin targeting agent diketo linker; compound 30). The branch point is in the connecting chain portion of the linker.

FIG. 4 shows a general scheme of an embodiment of a targeting agent-linker compound with a branched linker and two different targeting agents (Panel A) with a specific embodiment in Panel B (integrin targeting and folate targeting agent diketo linker; compound 31). The branch point is in the connecting chain portion of the linker.

FIG. 5 shows a general scheme of an embodiment of a targeting agent-linker compound with a branched linker and two different targeting agents (Panel A) with a specific embodiment in Panel B (integrin targeting agent diketo linker; compound 32). The branch point is in the recognition group portion of the linker.

FIG. 6 shows the structure of linker reactive groups. Structures A-C form reversible covalent bonds with reactive nucleophilic group (e.g. lysine or cysteine side chain) in the combining site of an antibody (structure A could form an irreversible covalent bond X is N and if $R_1$ and $R_3$ form part of a cyclic structure). $R_1$ and $R_2$ and $R_3$ in structures A-C represent substituents which can be C, H, N, O, P, S, Si, halogen (F, Cl, Br, I) or a salt thereof. X is N, C, Si, or any other heteroatom. These substituents may also include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R_2$ and $R_3$ could be cyclic as exemplified in structures B and C while X could be a heteroatom. Structures D-G form nonreversible covalent bonds with reactive nucleophilic group (e.g. lysine or cysteine side chain) in the combining site of an antibody. In these structures, $R_1$ and $R_2$ represent C, O N, halide and leaving groups such as mesyl or tosyl.

FIG. 7 shows various electrophiles suitable for reactive modification with a reactive amino acid side chain of an antibody. Key: (A) acyl beta-lactam; (B) simple diketone; (C) succinimide active ester; (D) maleimide; (E) haloacetamide with linker; (F) haloketone; (G) cyclohexyl diketone; and (H) aldehyde. R refers to other structure that may include a targeting agent, linker or antibody, while X refers to halogen.

FIG. 8 shows the structure of linker recognition group (Y), situated between the reactive group portion and the connecting chain portion of the linker. Panel A shows the relationship of the recognition group Y within the linker (see FIG. 2). Panels B-D show distance of Y from Z, substituents on the ring and ring member atoms.

FIG. 9 shows the structure of the linker connecting chain (X), which directly attaches at one end to the targeting agent as shown in Panel A (see FIG. 2). Substituents $R_2$ to $R_4$ are C, H, N, O, P, S, Si, halogen (F, Cl, Br, I) or a salt thereof, and may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl group, phosphoalkyl, phosphoalkenyl, phosphoalkynyl as well as a carbocyclic or heterocyclic mono or fused saturated or unsaturated ring structure. Panel B: R1 is O and R2 is C, H, N, O, P, S, Si, halogen (F, Cl, Br, I) or a salt thereof. In the connecting chain in structures B and C, n, r or m is 1-100. In structures D and E, n is 1, 2, 4, or more preferably is 3.

FIG. 10 shows Scheme 1, a synthetic scheme for the amine precursor of SCS-873, targeting agent 3 or SCS-amine. Key: (a) $BBr_3$, $CH_2Cl_2$, −20° C., 2 h; (b) DMF, rt to 80° C., 3 h; (c) BnCOCl, sat. aq. $NaHCO_3$, ether; (d) TBDPSiCl, imidazole, DMF, 16 h; (e) $Pd(OAc)_2$, (o-tol)$_3$P, i-$Pr_2$EtN, $CH_3CH_2CN$, reflux, 3 h; (f) 20% (w/w) Pd-C (10%), $H_2$, EtOH-AcOH (1:1), 36 h; (g) TBAF, THF, rt, 1 h; (h) DEAD, $PPh_3$, THF-benzene (3:1), 16 h; (i) 20% (w/w) Pd-C (10%), cyclohexene-i-PrOH (1:1), 90° C., 12 h; (j) i. aq. 2N NaOH, MeOH-THF (1:1), 16 h, ii. TFAA, anisole, $CH_2Cl_2$, 0° C., 2 h.

FIG. 11 shows Scheme 2, a synthetic scheme for making Compound 4, (R=Butoxycarboxyaminohexanoyl-derivative). Key: (a) DMF, rt; (b) EDC, HOBT, DMF; (c) 0.01 M in DMSO, 130° C.; (d) TFAA, anisole, dichloromethane; (e) DMF; (f) EDC, HOBT, DMF; (g) (i) step d, (ii) 2M NaOH, MeOH-THF (1:1).

FIG. 12 shows Scheme 3, a synthetic scheme for making compounds SCS-873 and SCS-1655.

FIG. 13 shows Scheme 4, a synthetic scheme for making Compounds SCS-864 and SCS-789. Key: (a) $Et_3N$, DMF, rt, 16h.

DETAILED DESCRIPTION OF THE INVENTION

Figure 2:
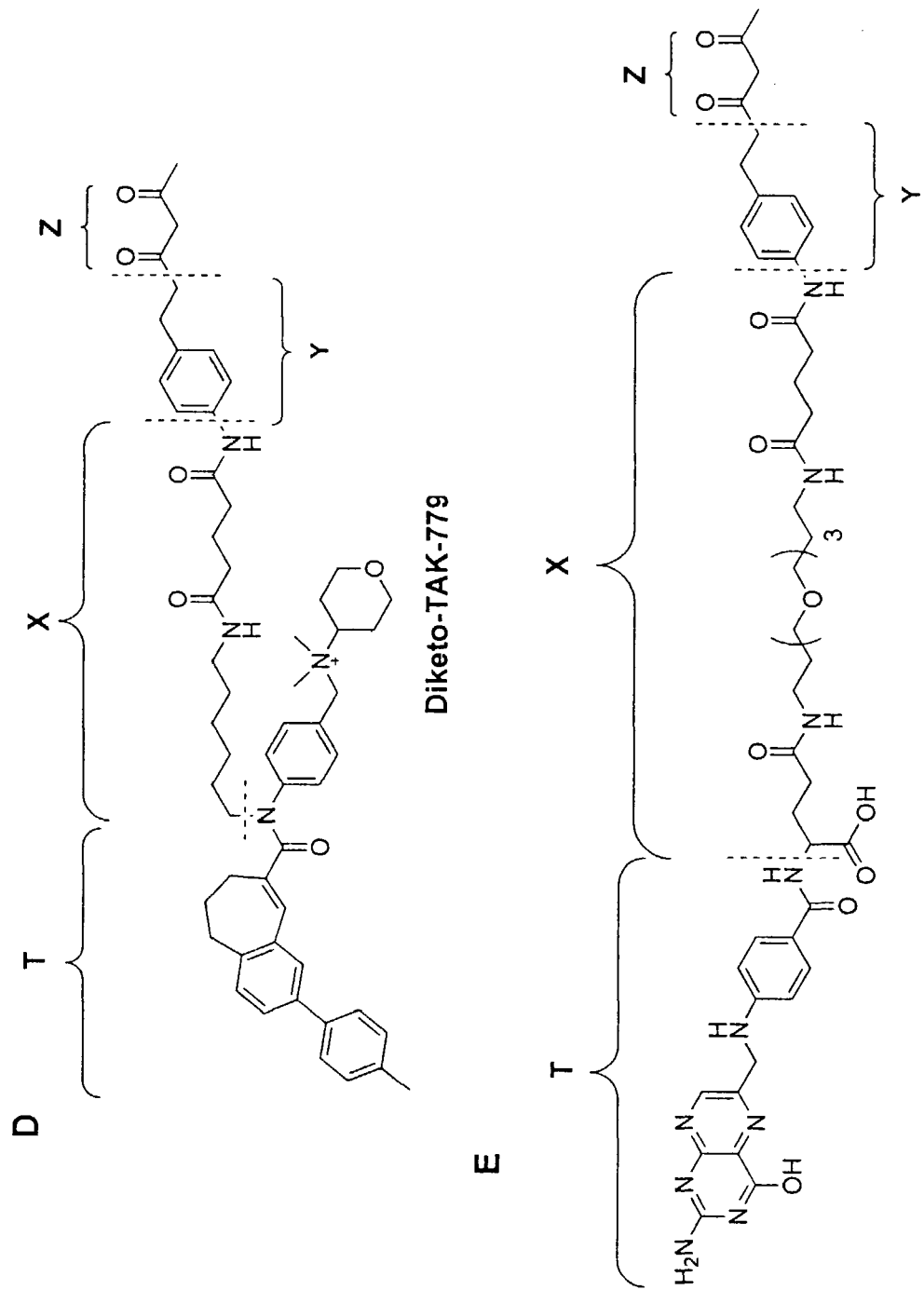
FIG. 2 shows a general scheme of a targeting agent-linker compound with a non-branched linker (Panel A) with specific embodiments in Panel B (SCS-873), Panel C (PST inhibitor diketo linker; compound 26), Panel D (TAK-799 diketo linker; compound 27) and Panel E (folate ligand dikone linker; compound 28).

The present invention provides various antibody targeting compounds in which targeting agents and/or biological agents are covalently or noncovalently linked to the combining site of an antibody. When one or more targeting agents are linked, at least one of the targeting agents will be linked so that it can bind its target. This may be achieved by linking the targeting agent in a manner that does effect its binding specificity for the target and by sufficiently distancing the targeting agent from the antibody combining site so that it can bind its target without steric hindrance by the antibody. This may be achieved by using a suitable linker and linking strategy discussed in more detail ahead.

When a biological agent is not also a targeting agent it is preferred that the antibody retain at least some antigen binding specificity following linkage to one or more biological agents. The antibody compound in which one or more biological agents are linked to the antibody combining site may exhibit biological activity due to a linked biological agent if such agent is biologically active while linked to the antibody. This may be achieved by various strategies such as by linking the antibody combining site to a location on the biological agent that does not affect biological activity. Another strategy is to position the biological agent away from the antibody so that the biological agent can bind to another molecule necessary for activity without steric hindrance by the antibody. Other strategies for obtaining a biological activity of one or more biological agents linked to the antibody combining site are well known to the skilled artisan. In some embodiments, the biological activity of a biological agent may not be realized until the agent is released from the antibody combining site. This may be achieved in some embodiments though the aid of labile linkage as discussed further ahead.

In some embodiments, the native antigen binding specificity of the antibody which exists before covalent linkage will not be substantially modified following covalent linkage. In other words, the antibody compound resulting from covalent linkage of one or more targeting agents or one or more biological agents may bind the same antigens with a similar affinity as it did prior to covalent linkage. In other embodiments, the binding specificity of the antibody before covalent linkage will be substantially modified following covalent linkage. Substantially modified antibody binding specificity resulting from covalent linkage may be due to a substantially reduced ability of the covalently linked antibody to bind to an antigen or a substantially increased ability of the covalently linked antibody to bind to an antigen. In some embodiments, binding of the antigen binding site to antigen is sufficiently reduced such that the original antigen binding specificity of the antibody is effectively eliminated. In some embodiments, the antigen binding site to antigen is sufficiently reduced such that the original antigen binding specificity of the antibody is effectively eliminated and replaced with that of a targeting agent(s) covalently linked to the antibody combining site. In embodiments where the binding specificity of the antibody is effectively replaced with that of the targeting agent(s), the antibody, after covalent linkage to the targeting agent(s), exhibits an affinity for the target molecule of greater than about $1\times10^{-6}$ moles/liter.

Although not wishing to be bound by any theory, substantially reduced antibody binding to antigen may result from the targeting agent(s) or biological agent(s) sterically hindering the antigen from contacting the antibody combining site. Alternatively, or in addition, substantially reduced antigen binding may result if the amino acid side chain of the antibody combining site modified by covalent linkage was important for binding to the antigen. Substantially increased antibody binding to an antigen may result when the targeting agent(s) or biological agent(s) do not sterically hinder the antigen from contacting the antibody combining site and amino acid side chain of the antibody combining site modified by covalent linkage was important for binding to the antigen.

The targeting compounds of the invention may comprise an antibody or an antibody fragment that has a single combining site such as Fab or Fab' antibody fragments. In such cases, the targeting agent will be linked to the single combining site of that antibody molecule. If an antibody or antibody fragment of a targeting molecule comprises two or more combining sites, at least one of the combining sites will include a covalently linked targeting agent. In some cases, all or most of the combining sites of an antibody can be covalently linked to a targeting agent. If multiple combining sites of an antibody are to be linked to targeting agents, the combining sites may all have the same targeting agent linked thereto or may have different targeting agents linked to the same antibody. It would be readily understood that one could covalently link multiple targeting agents to a single antibody combining site. Such multimeric targeting agents may be heteromultimeric or homomultimeric with respect to the specificity of the targeting agents in the multimer.

"Targeting agent" or "targeting component" as used herein refers to a moiety that recognizes, binds or adheres to a target moiety of a target molecule located for example in a cell, tissue (e.g. extracellular matrix), fluid, organism, or subset thereof. A targeting agent and its target molecule represent a binding pair of molecules, which interact with each other through any of a variety of molecular forces including, for example, ionic, covalent, hydrophobic, van der Waals, and hydrogen bonding, so that the pair have the property of binding specifically to each other. Specific binding means that the binding pair exhibit binding with each other under conditions where they do not bind to another molecule. Examples of binding pairs are biotin-avidin, hormone-receptor, receptor-ligand, enzyme-substrate, lgG-protein A, antigen-antibody, and the like. The targeting agent and its cognate target molecule exhibit a significant association for each other. This association may be evaluated by determining an equilibrium association constant (or binding constant) according to methods well known in the art. Affinity is calculated as $K_d=k_{off}/k_{on}$ ($k_{off}$ is the dissociation rate constant, $k_{on}$ is the association rate constant and $K_d$ is the equilibrium constant.

Affinity can be determined at equilibrium by measuring the fraction bound (r) of labeled ligand at various concentrations (c). The data are graphed using the Scatchard equation: $r/c=K(n-r)$:

where r=moles of bound ligand/mole of receptor at equilibrium;

c=free ligand concentration at equilibrium;

K=equilibrium association constant; and n=number of ligand binding sites per receptor molecule By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat No. 6,316,409). The affinity of a targeting agent for its target molecule is preferably at least about $1\times10^{-6}$ moles/liter, is more preferably at least about $1\times10^{-7}$ moles/liter, is even more preferably at least about $1\times10^{-8}$ moles/liter, is yet even more preferably at least about $1\times10^{-9}$ moles/liter, and is most preferably at least about $1\times10^{-10}$ moles/liter.

Targeting agents include, but are not limited to, small molecule organic compounds of 5,000 daltons or less such as drugs, proteins, peptides, peptidomimetics, glycoproteins, proteoglycans, lipids glycolipids, phospholipids, lipopolysaccharide, nucleic acids, proteoglycans, carbohydrates, and the like. Targeting agents may include well known therapeutic compounds including anti-neoplastic agents. Anti-neoplastic targeting agents may include targpaclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin, and the like. Antimicrobial agents include aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, anti-parasitic compounds such as antimonials, and the like. Hormone targeting agents include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

In some preferred embodiments, the targeting agent is not an antibody. In other preferred embodiments, the targeting agent is not a metal chelate. Preferably, the targeting agent is a small molecule as compared with a native immunoglobulin. The targeting agent, including any linking moiety necessary for covalently linking the targeting agent to an amino acid residue of the antibody combining site, preferably is at least about 300 daltons in size, and preferably may be at least about 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500 or even 5,000 daltons in size, with even larger sizes possible.

Suitable targeting agents in targeting compounds of the invention can be a protein or peptide. "Polypeptide", "peptide," and "protein" are used interchangeably to refer to a polymer of amino acid residues. As used herein, these terms apply to amino acid polymers in which one or more amino acid residue is an artificial chemical analogue of a corresponding naturally occurring amino acid. These terms also apply to naturally occurring amino acid polymers. Amino acids can be in the L or D form as long as the binding function of the peptide is maintained. Peptides can be of variable length, but are generally between about 4 and 200 amino acids in length. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

Protein or peptide targeting agents that exhibit binding activity for a target molecule are well known in the art. For example, a targeting agent may be a viral peptide cell fusion inhibitor. This may include the T-20 HIV-1 gp41 fusion inhibitor which targets fusion receptors on HIV infected cells (for T-20, see U.S. Pat. Nos. 6,281,331 and 6,015,881 to Kang et al.; Nagashima et al. J. Infectious Diseases 183:1121, 2001; for other HIV inhibitors see U.S. Pat. No. 6020459 to Barney and WO 0151673A2 to Jeffs et al), RSV cell fusion inhibitors (see WO 0164013A2 to Antczak and McKimm-Breschkin, Curr. Opin. Invest. Drugs 1:425-427, 2000 (VP-14637)), pneumovirus genus cell fusion inhibitors (see WO 9938508A1 by Nitz et al.), and the like. Targeting agents also include peptide hormones or peptide hormone analogues such as LHRH, bombesin/gastrin releasing peptide, somatastatin (e.g., RC-121 octapeptide), and the like, which may be used to target any of a variety of cancers ovarian, mammary, prostate small cell of the lung, colorectal, gastric, and pancreatic. See, e.g., Schally et al., Eur. J. Endocrinology, 141: 1-14, 1999.

Peptide targeting agents suitable for use in targeting compounds of the invention also may be identified using in vivo targeting of phage libraries that display a random library of peptide sequences (see, e.g., Arap et al., Nature Medicine, 2002 8(2):121-7; Arap et al., Proc. Natl. Acad. Sci. USA 2002 99(3):1527-1531; Trepel et al. Curr. Opin. Chem. Biol. 2002 6(3):399-404).

In some embodiments, the targeting agent is specific for an integrin. Integrins are heterodimeric transmembrane glycoprotein complexes that function in cellular adhesion events and signal transduction processes. Integrin $\alpha_v\beta_3$ is expressed on numerous cells and has been shown to mediate several biologically relevant processes, including adhesion of osteoclasts to bone matrix, migration of vascular smooth muscle cells, and angiogenesis. Integrin $\alpha_v\beta_3$ antagonists likely have use in the treatment of several human diseases, including diseases involving neovascularization, such as rheumatoid arthritis, cancer, and ocular diseases.

Suitable targeting agents for integrins include RGD peptides or peptidomimetics or non-RGD peptides or peptidomimetics. As used herein, reference to "Arg-Gly-Asp peptide" or "RGD peptide" is intended to refer to a peptide having one or more Arg-Gly-Asp containing sequence which may function as a binding site for a receptor of the "Arg-Gly-Asp family of receptors", e.g., an integrin. Integrins, which comprise and alpha and abeta subunit, include numerous types including $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_L\beta_1$, $\alpha_6\beta_4$, $\alpha_4\beta_7$, $\alpha_D\beta_2$, $\alpha_D\beta_2$, $\alpha_L\beta_2$, $\alpha_M\beta_2$, $\alpha_v\beta_1$, $\alpha_v\beta_3$, $\alpha_v\beta_5$, $\alpha_v\beta_6$, $\alpha_v\beta_8$, $\alpha_v\beta_2$, $\alpha_{IIb}\beta_3$, $\alpha_{IELb}\beta_7$, and the like. The sequence RGD is present in several matrix proteins and is the target for cell binding to matrix by integrins. Platelets contain a large amount of RGD-cell surface receptors of the protein GP $II_b/III_a$, which is primarily responsible, through interaction with other platelets and with the endothelial surface of injured blood vessels, for the development of coronary artery thrombosis. The term RGD peptide also includes amino acids that are functional equivalents (e.g., RLD or KGD) thereof provided they interact with the same RGD receptor. Peptides containing RGD sequences can be synthesized from amino acids by means well known in the art, using, for example, an automated peptide synthesizer, such as those manufactured by Applied Biosystems, Inc., Foster City, Calif.

As used herein, "non-RGD" peptide refers to a peptide that is an antagonist or agonist of integrin binding to its ligand (e.g. fibronectin, vitronectin, laminin, collagen etc.) but does not involve an RGD binding site. Non-RGD integrin peptides are known for $\alpha_v\beta_3$ (see, e.g., U.S. Pat. Nos. 5,767,071 and 5,780,426) as well as for other integrins such as $\alpha_4\beta_1$ (VLA-4), $\alpha_4\beta_7$ (see, e.g., U.S. Pat. No. 6,365,619; Chang et al., Bioorganic & Medicinal Chem Lett, 12:159-163 (2002); Lin et al., Bioorganic & Medicinal Chem Lett, 12:133-136 (2002)), and the like.

An integrin targeting agent may be a peptidomimetic agonist or antagonist, which preferably is a peptidomimetic agonist or antagonist of an RGD peptide or non-RGD peptide. As used herein, the term "peptidomimetic" is a compound containing non-peptidic structural elements that are capable of mimicking or antagonizing the biological action(s) of a natural parent peptide. A peptidomimetic of an RGD peptide is an organic molecule that retains similar peptide chain pharmacophore groups of the RGD amino acid sequence but lacks amino acids or peptide bonds in the binding site sequence. Likewise, a peptidomimetic of a non-RGD peptide is an organic molecule that retains similar peptide chain pharmacophore groups of the non-RGD binding site sequence but lacks amino acids or peptide bonds in the binding site sequence. A "pharmacophore" is a particular three-dimensional arrangement of functional groups that are required for a compound to produce a particular response or have a desired activity. The term "RGD peptidomimetic" is intended to refer to a compound that comprises a molecule containing the RGD pharmacophores supported by an organic/non-peptide structure. It is understood that an RGD peptidomimetic (or non-RGD peptidomimetic) may be part of a larger molecule that itself includes conventional or modified amino acids linked by peptide bonds.

RGD peptidomimetics are well known in the art, and have been described with respect to integrins such as GPIIb/IIIa, $\alpha_v\beta_3$ and $\alpha_v\beta_5$ (See, e.g., Miller et al., J. Med. Chem. 2000, 43:22-26; and International Patent Publications WO 0110867, WO 9915178, WO 9915170, WO 9815278, WO 9814192, WO 0035887, WO 9906049, WO 9724119 and WO 9600730; see also Kumar et al., Cancer Res. 61:2232-2238 (2000)). Many such compounds are specific for more than one integrin. RGD peptidomimetics are generally based on a core or template (also referred to as "fibrinogen receptor antagonist template"), to which are linked by way of spacers to an acidic group at one end and a basic group at the other end of the core. The acidic group is generally a carboxylic acid functionality while the basic group is generally a N-containing moiety such as an amidine or guanidine. Typically, the core structure adds a form of rigid spacing between the acidic moiety and the basic nitrogen moiety, and contains one or more ring structures (e.g., pyridine, indazole, etc.) or amide bonds for this purpose. For a fibrinogen receptor antagonist, generally, about twelve to fifteen, more preferably thirteen or fourteen, intervening covalent bonds are present (via the shortest intramolecular path) between the acidic group of the RGD peptidomimetic and a nitrogen of the basic group. The number of intervening covalent bonds between the acidic and basic moiety is generally shorter, two to five, preferably three or four, for a vitronectin receptor antagonist. The particular core may be chosen to obtain the proper spacing between the acidic moiety of the fibrinogen antagonist template and the nitrogen atom of the pyridine. Generally, a fibrinogen antagonist will have an intramolecular distance of about 16 angstroms (1.6 nm) between the acidic moiety (e.g., the atom which gives up the proton or accepts the electron pair) and the basic moiety (e.g., which accepts a proton or donates an electron pair), while a vitronectin antagonist will have about 14 angstroms (1.4 nm) between the respective acidic and basic centers. Further description for converting from a fibrinogen receptor mimetic to a vitronectin receptor mimetic can be found in U.S. Pat. No. 6,159,964.

The peptidomimetic RGD core can comprise a 5-11 membered aromatic or nonaromatic mono- or polycyclic ring system containing 0 to 6 double bonds, and containing 0 to 6 heteroatoms chosen from N, O and S. The ring system may be unsubstituted or may be substituted on a carbon or nitrogen atom. Preferred core structures with suitable substituents useful for vitronectin binding include monocyclic and bicyclic groups, such as benzazapine described in WO 98/14192, benzdiazapine described in U.S. Pat. No. 6,239,168, and fused tricyclics described in U.S. Pat. No. 6,008,213.

U.S. Pat. No. 6,159,964 contains an extensive list of references in Table 1 of that document which disclose RGD peptidomimetic cores structures (referred to as fibrinogen templates) which can be used for prepraring RGD peptidomimetics. Preferred vitronectin RGD and fibronectin RGD peptidomimetics are disclosed in U.S. Pat. Nos. 6,335,330; 5,977,101; 6,088,213; 6,069,158; 6,191,304; 6,239,138; 6,159,964; 6,117,910; 6,117,866; 6,008,214; 6,127,359; 5,939,412; 5,693,636; 6,403,578; 6,387,895; 6,268,378; 6,218,387; 6,207,663; 6,011,045; 5,990,145; 6,399,620; 6,322,770; 6,017,925; 5,981,546; 5,952,341; 6,413,955; 6,340,679; 6,313,119; 6,268,378; 6,211,184; 6,066,648; 5,843,906; 6,251,944; 5,952,381; 5,852,210; 5,811,441; 6,114,328; 5,849,736; 5,446,056; 5,756,441; 6,028,087; 6,037,343; 5,795,893; 5,726,192; 5,741,804; 5,470,849; 6,319,937; 6,172,256; 5,773,644; 6,028,223; 6,232,308; 6,322,770; 5,760,028.

Exemplary RGD peptidomimetic integrin targeting agents are shown below as compounds 1, 2, and 3 can be used for preparing an intregrin targeting compound of the present invention. In the three compounds, the linker is attached as indicated to the nitrogen of the seven membered ring. Other RGD peptidomimetic integrin targeting agents include compound 33, wherein P and L or carbon or nitrogen. The linker may be R1 or R2 while the R3 group includes a basic group such as an —NH group. In some embodiments, the R3 group is as shown in compounds 1, 2, or 33. In some embodiments, the R3 group includes a heterocyclic group such a benzimidazole, imidazole, pyridine group, or the like. In some such embodiments, the R3 group is a alkoxy group, such as a propoxy group or the like, that is substituted with a heterocyclyl group that is substituted with an alkylamine group, such as a methylamino group or the like, whereas in other embodiments, the R3 group is an alkoxy group, such as a propoxy group or the like, substituted with a heterocyclylamino group, such as with a pyridinylamino group or the like such as a 2-pyridinylamino group. In other embodiments R3 is a group of formula —C(=O)Rb where Rb is selected from —N(alkyl)-alkyl-heterocyclyl groups such as —N(Me)—CH2-benzimidazole groups and the like.

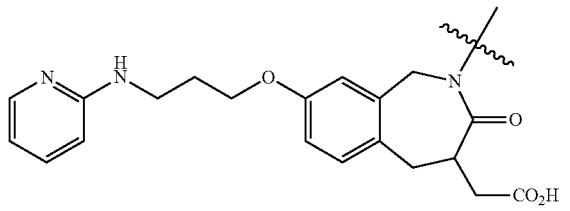

1

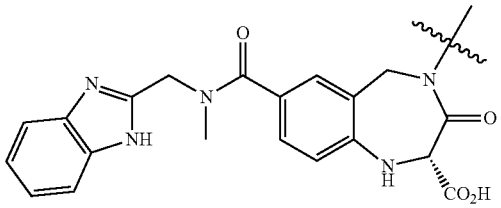

2

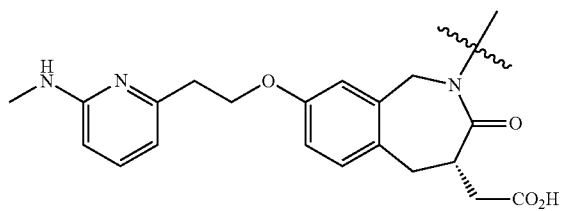

3

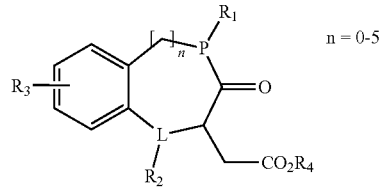

33 n = 0-5

Other exemplary integrin peptidomimetic targeting agents and a peptide targeting agent are shown in FIG. 1. The linker may be any of $R_1$, $R_2$, $R_3$, while $R_4$ may be a linker or a hydrolyzable group such as alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group, and the like. One of skill in the art will readily appreciate that other integrin agonist and antagonist mimetics can also be used in targeting compounds of the present invention.

The target molecule to which the targeting agent of the targeting compound binds is preferably a non-immunoglobulin molecule or is an immunoglobulin molecule where the target moiety is outside the immunoglobulin combining site. It is not intended to exclude from the inventive compounds those targeting agents that function as antigens and, therefore, bind to an immunoglobulin combining site. Such targeting agents are included herein provided the targeting agents also bind to a non-immunoglobulin molecule and/or a target moiety located outside the combining site of an immunoglobulin molecule. In general, the target molecule can be any type of molecule including organic, inorganic, protein, lipid, carbohydrate, nucleic acid and the like.

The target molecule is preferably a biomolecule such as a protein, carbohydrate, lipid or nucleic acid. The target molecule can be associated with a cell ("cell surface expressed"), or other particle ("particle surface expressed") such as a virus, or may be extracellular. If associated with a cell or particle, the target molecule is preferably expressed on the surface of the cell or particle in a manner that allows the targeting agent of the targeting compound to make contact with the surface receptor from the fluid phase of the body.

In some preferred embodiments, the target molecule is predominantly or exclusively associated with a pathological condition or diseased cell, tissue or fluid. Thus, the targeting agent of a present antibody targeting compound can be used to deliver the targeting compound to a diseased tissue by targeting the cell, an extracellular matrix biomolecule or a fluid biomolecule. Exemplary target molecules disclosed hereinafter in the Examples include integrins (Example 1), cytokine receptors (Examples 2, 3 and 7), cytokines (Example 4), vitamin receptors (Example 5), cell surface enzymes (Example 6), and HIV-1 virus and HIV-1 virus infected cells (Examples 8 and 11), and the like.

In other preferred embodiments, the target molecule is associated with an infectious agent and is expressed on the surface of a microbial cell or on the surface of a viral particle. As such, antibody targeting compositions in which the targeting agent can bind to the cell surface expressed or particle expressed infectious agent can be used as an anti-microbial, by targeting microbial agents inside the body or on the surface (e.g., skin) of an individual. In the latter case, the invention compound can be applied topically.

Antibody targeting agents specific for a microbial target molecule also can be used as an anti-microbial agent in vitro. Accordingly, a method of reducing the infectivity of microbial cells or viral particles present on a surface is provided. Some methods include contacting the surface of a microbial cell or viral particle with an effective amount of the invention targeting compound. The targeting compound in such methods includes a targeting agent specific for a receptor on the microbial cell or virus particle. Applicable surfaces are any surfaces in vitro such as a counter top, condom, and the like.

Another preferred target molecule for targeting molecules of the invention is prostate specific antigen (PSA), a serine protease that has been implicated in a variety of disease states including prostate cancer, breast cancer and bone metastasis. Specific inhibitors of PSA which bind to the active site of PSA are known. See Adlington et al., J. Med. Chem., 2001, 44:1491-1508 and WO 98/25895 to Anderson. A specific inhibitor of PST is shown below as compound 34.

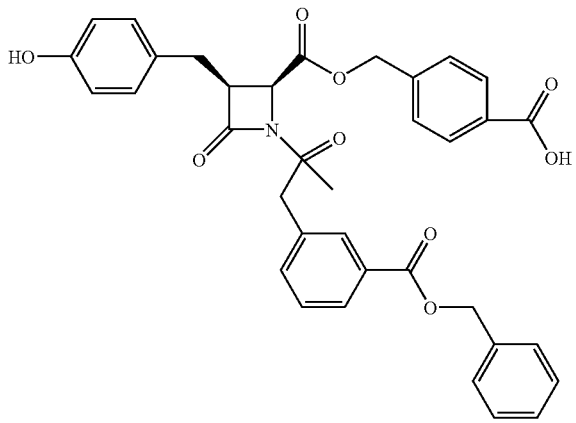

34

A targeting agent, in addition to its ability to bind a target molecule, may be characterized in having one or more biological activities, each activity characterized as a detectable biological affect on the functioning of a cell organ or organism. Thus, in addition to being a targeting agent, such compounds can be considered biological agents. For example, the integrin targeting agents shown as compounds 1, 2, 3 and 33 above not only target an integrin, but have integrin antagonist biological activity. In some embodiments, however, a targeting agent may be a pure binding agent without biological activity.

The targeting compounds of the invention include a targeting agent that is covalently linked to a combining site of an antibody. Such targeting compounds may have one or more biological activities associated with the targeting compound. The biological activity may be an inherent feature of the targeting agent itself or may be provided by a biological agent distinct from the targeting agent in the targeting compound. The biological agent may be associated covalently or non-covalently with the other molecules or portions of the targeting compound, although covalent linkage is preferred. The biological agent may be linked to either the targeting agent, the antibody, or both by means well known in the art. For example, see Kiaris et al., Eur. J. Cancer 37:620-628 (2001) and Schally et al. Eur. J. Endocrin. 141:1-14 (1989), which describe various conjugates between peptide hormone targeting agents and doxorubicin. See also, Canevari et al., Ann Oncol Oct. 5, 1994 (8):698-701; Rihova, Folia Microbiol (Praha) 1995;40(4):367-84; Vitetta, Princess Takamatsu Symp 1988;19:333-40; and Ghose et al., Crit Rev Ther Drug Carrier Syst 1987;3(4):263-359. Thus, in some embodiments, the antibody-targeting agent targeting compounds of the invention may include a functional component in the form of a targeting agent that has inherent biological activity. In such embodiments, the targeting agent is linked to a combining site of the antibody or antibody fragment and the targeting agent is the functional component that exhibits the biological activity. In other embodiments, the targeting compound includes a targeting agent linked to a combining site of an antibody or antibody fragment, and also includes a separate functional component that is preferably attached or linked to the targeting compound through a covalent bond.

A targeting agent or biological agent can be linked to an antibody targeting compound of the invention using a linkage that is labile under certain conditions. The labile linkage may be between the antibody and the targeting agent or biological agent, while if a linker is present, the labile linkage may be between the antibody and the linker, the targeting agent or biological agent and the linker, within the linker, or combinations thereof.

Labile linkers include, reversible covalent bonds, pH sensitive linkages (acid or base sensitive), enzyme sensitive linkages, degradation sensitive linkers, photosensitive linkers, sand the like, and combinations thereof. These features are also characteristic of a prodrug which can be considered as a type of labile linker. A variety of labile linkers have been previously designed. For example, prodrugs can be formed using compounds having carboxylic acid moieties that slowly degrade by hydrolysis as described in U.S. Pat. No. 5,498,729.

The particular design of a labile linker may be used to direct release of the biological agent after it has reached the intended target. For example, a linkage may be designed to direct release in a particular intracellular compartment or in an extracellular compartment in which antibody targeting compounds may accumulate. An acid-labile linker such as a cis-aconitic acid linker can take advantage of the acidic environment of different intracellular compartments such as the endosomes encountered during receptor mediated endocytosis and the lysosomes. See Shen et al., Biochem. Biophys. Res. Commun. (1981) 102:1048-1054; Yang et al., J. Natl.

Canc. Inst. (1988) 80: 1154-1159. A peptide spacer arm located within or at the ends of a linker can be used to effect release of a targeting agent or biological agent by the action of a peptidase such as a lysosomal peptidase. See e.g., Trouet et al., Proc. Natl. Acad. Sci. (1982) 79: 626-629.

Particular targeting agents may or may not possess biological activity depending on the context of their use. For example, the therapeutic drug doxorubicin, which is a DNA intercalator, can be a targeting agent for double stranded DNA when the drug is covalently linked to an antibody and applied to DNA in a cell-free form. Doxorubicin, however, may not be considered a targeting agent with respect to a cell while the drug is covalently linked to an antibody unless the compound can be taken up by the cell. In the latter case, doxorubicin may have biological activity following uptake if the drug can access DNA in the cell nucleus.

Biological agent functional components include, but are not limited to, small molecule drugs (a pharmaceutical organic compound of about 5,000 daltons or less), organic molecules, proteins, peptides, peptidomimetics, glycoproteins, proteoglycans, lipids glycolipids, phospholipids, lipopolysaccharides, nucleic acids, proteoglycans, carbohydrates, and the like. Biological agents may be anti-neoplastic, anti-microbial, a hormone, an effector, and the like. Such compounds include well known therapeutic compounds such as the anti-neoplastic agents paclitaxel, daunorubicin, doxorubicin, carminomycin, 4'-epiadriamycin, 4-demethoxydaunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin, and the like. Anti-microbial agents include aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, anti-parasitic compounds such as antimonials, and the like. Hormones may include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, hormone receptors such as the estrogen receptor. Also included are non-steroidal anti-inflammatories such as indomethacin, salicylic acid acetate, ibuprofen, sulindac, piroxicam, and naproxen, and anesthetics or analgesics. Also included are radioisotopes such as those useful for imaging as well as for therapy.

Biological agent functional components for use in the targeting compounds of the invention can be naturally occurring or synthetic. Biological agents can be biologically active in their native state, or be biologically inactive or in a latent precursor state and acquire biological or therapeutic activity when a portion of the biological agent is hydrolyzed, cleaved or is otherwise modified. The prodrug can be delivered at the surface of a cell or intracellulary using antibody targeting compounds of the invention where it can then be activated. In this regard, the biological agent can be a "prodrug," meaning that prodrug molecules capable of being converted to drugs (active therapeutic compounds) by certain chemical or enzymatic modifications of their structure. In the prodrug approach, site-specific drug delivery can be obtained from tissue-specific activation of a prodrug, which is the result of metabolism by an enzyme that is either unique for the tissue or present at a higher concentration (compared with other tissues); thus, it activates the prodrug more efficiently.

Photodynamic treatment may be used to activate a prodrug by cleaving a photosenitive linker or by activating a photoresponsive enzyme (acyl enzyme hydrolysis) as described previously (see U.S. Pat. Nos. 5,114,851 and 5,218,137). Photodynamic treatment also may be used to rapidly inactivate a drug in sites where the drug activity is not desired (e.g. in non-target tissues). Various means of covalently modifying a drug to form a prodrug are well known in the art.

Targeting agents may be covalently linked to the antibody combining site directly or through the aid of a linker. An appropriate linker can be chosen to provide sufficient distance between the targeting agent and the antibody combining site in order for the targeting agent to be able to bind to its target molecule. This distance depends on several factors including, for example, the distance from the outermost surface of the antibody combining site to the reactive side chain in the combining site, and the nature of the targeting agent. Generally, the linker will be between about 5 to 10 angstroms (0.5 to 1 nm) in length, with 10 or more angstroms (1.0 nm) being more preferred, although shorter linkers of about 3 angstroms (0.3 nm) in length may be sufficient if the amino acid side chain is very near to the outermost portion of the combining site and/or the targeting agent or biological agent includes a segment that can function as a part of a linker.

Linker length may also be viewed in terms of the number of linear atoms (cyclic moieties such as aromatic rings and the like to be counted by taking the shortest route). Linker length under this measure is generally about 10 to 200 atoms and more typically about 30 or more atoms, although shorter linkers of two or more atoms may be sufficient if the reactive amino acid side chain is very near to the outermost portion of the combining site. Generally, linkers with a linear stretch of at least about 9 atoms are sufficient. Other linker considerations include effect on physical or pharmacokinetic properties of the resulting targeting compound or targeting agent-linker, solubility, lipophilicity, hydrophilicity, hydrophobicity, stability (more or less stable as well as planned degradation), rigidity, flexibility, immunogenicity, modulation of antibody binding, chemical compatibility with targeting agent, ability to be incorporated into a micelle or liposome, and the like.

In targeting compounds where a linker is present between the antibody combining site, the targeting agent may be prepared by several approaches. In one approach, a targeting agent-linker compound and/or biological agent-linker compound is synthesized with a linker that includes one or more reactive groups designed for covalent reaction with a side chain of an amino acid in the combining site of an antibody. The agent-linker compound and antibody are combined under conditions where the linker reactive group forms a covalent bond with the amino acid side chain.

In another approach, linking can be achieved by synthesizing an antibody-linker compound comprising an antibody and a linker wherein the linker includes one or more reactive groups designed for covalent reaction with an appropriate chemical moiety of the targeting agent or biological agent. The targeting agent or biological agent may need to be modified to provide the appropriate moiety for reaction with the linker reactive group. The antibody-linker and targeting agent and/or biological agent are combined under conditions where the linker reactive group covalently links to the targeting and/or biological agent.

A further approach for forming an antibody targeting compound of the invention uses a dual linker design. In one embodiment, the an agent-linker compound is synthesized which comprises a targeting agent and/or a biological agent and a linker with a reactive group. An antibody-linker compound is synthesized which comprises an antibody and a linker with a chemical group susceptible to reactivity with the reactive group of the agent-linker of the first step. These two linker containing compounds are then combined under conditions whereby the linkers covalently link, forming the antibody targeting compound.

In another embodiment, an antibody-linker compound is synthesized which comprises an antibody and a linker with a reactive group. A targeting agent and/or biological agent-linker compound is prepared which comprises the agent and a linker with a chemical group susceptible to reactivity with the reactive group of the antibody-linker of the first step. These two linker containing compounds are then combined under conditions whereby the linkers covalently link, forming the antibody targeting compound. "Susceptible" as used herein with reference to a chemical moiety indicates that the chemical moiety will covalently bond with a compatible reactive group. Thus, an electrophilic group is susceptible to covalent bonding with a nucleophillic group and vice versa.

As discussed, the linker may be first conjugated to the targeting agent and then the targeting agent-linker conjugated to the antibody combining site. Alternatively, the linker may be conjugated first to the antibody combining site and the antibody-linker conjugated to the targeting agent. Numerous means well known in the art can be used to attach a linker to the targeting agent or antibody combining site. Exemplary functional groups that can be involved in the linkage include, for example, esters, amides, ethers, phosphates, amino, keto, amidine, guanidine, imines, eneamines, phosphates, phosphonates, epoxides, aziridines, thioepoxides, masked or protected diketones (ketals for example), lactams, haloketones, aldehydes, thiocarbamate, thioamide, thioester, sulfide, disulfide, phosphoramide, sulfonamide, urea, thioruea, carbamate, carbonate, hydroxamide, and the like.

The linker includes any atom from the group C, H, N, O, P, S, Si, halogen (F, Cl, Br, I) or a salt thereof. The linker also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. The linker also may include one or more ring structures. As used herein a "ring structure" includes a carbocyclic homo or hetero mono or fused saturated or unsaturated ring structure. Combinations of the above groups and rings may also be present in the linkers of the targeting compounds of the invention.

The general design of a embodiment of a unbranched linker for use in preparing targeting compounds of the present invention is shown in FIG. 2A. The linker is of the formula

X—Y—Z

Wherein X is a connecting chain, Y is a recognition group and Z is a reactive group. FIGS. 2B-E shows various targeting agent-linker compounds with the linker X, Y and Z portions identified. The linker may be linear or branched. In some embodiments, the linker has a linear stretch of between 5-200 or 10-200 atoms although in other embodiments, longer linker lengths may be used. One or more targeting agents may be linked to X. In some embodiments, where more than one targeting agent is linked and a branched linker is used, some of the targeting agents may be linked to different branches of the linker. However, it should be understood that linkers used in the compounds of the invention may have one or more recognition groups, one or more reactive groups and one or more connecting chains and combinations thereof. Connecting chains may branch from another connecting chain or from a recognition group.

The connecting chain X of the linker includes any atom from the group C, H, N, O, P, S, Si, halogen (F, Cl, Br, I) or a salt thereof. X also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. In some embodiments, X may include one or more ring structures. In a preferred embodiment, X includes a repeating ether unit of between 2-100 units. Various embodiments of X are shown in FIG. 9.

The recognition group Y of the linker is optional and if present is located between the reactive group and the connecting chain. In preferred embodiments, Y is located from 1-20 atoms from Z. Although not wishing to be bound by any theory, it is believed that the recognition group acts to properly position the reactive group into the antibody combining site so that it may react with a reactive amino acid side chain. FIG. 8 shows a variety of exemplary recognition groups with one or more homo or hetero ring structures of five or six atoms. Larger ring structures also may be used. One or more targeting agents may be linked to Y. In some embodiments, a linker may be used to link the targeting agent to Y. In embodiments where two or more targeting agents are used, one or more can be attached to both X and Y. More than one targeting agent also can be attached to Y.

The linker reactive group Z includes any nucleophilic or electrophilic group. In a preferred embodiment Z is capable of forming a covalent bond with a reactive side chain of an antibody. In some embodiments, Z includes one or more C=O, groups arranged to form a diketone, an acyl beta-lactam, an active ester, haloketone, a cyclohexyl diketone group, an aldehyde or maleimide. Other groups may include lactone, anhydride, and alpha-haloacetamide or an epoxide. Exemplary linker electrophilic reactive groups that can covalently bond to a reactive nucleophilic group (e.g. lysine or cysteine side chain) in the combining site of an antibody include acyl beta-lactam, simple diketone, succinimide active ester, maleimide, haloacetamide with linker, haloketone, cyclohexyl diketone, aldehyde, amidine, guanidine, imine, eneamine, phosphate, phosphonate, epoxide, aziridine, thioepoxide, a masked or protected diketone (a ketal for example), lactam, sulfonate, and the like masked C=O groups such as imine, ketal, acetal and any other known electrophilic group. A preferred linker reactive group includes one or more C=O, groups arranged to form a acyl beta-lactam, simple diketone, succinimide active ester, maleimide, haloacetamide with linker, haloketone, cyclohexyl diketone, or aldehyde.

Z may be a group that forms a reversible or nonreversible covalent bond. In some embodiments, reversible covalent bonds may be formed using diketone Z groups such as those shown in FIG. 6. $R_1$ and $R_2$ and $R_3$ in structures A—C of FIG. 6 represent substituents which can be C, H, N, O, P, S, Si, halogen (F, Cl, Br, I) or a salt thereof. These substituents also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R_2$ and $R_3$ also could from a ring structure as exemplified in structures B and C. X in FIG. 6 could be a heteroatom. Other Z groups that form reversible covalent bonds include the diketone amidine, imine, and other reactive groups shown in structures B and G of FIG. 7. FIG. 7 also includes the structures of other preferred linker reactive groups.

Z reactive groups that form a nonreversible covalent bond with the combining site of an antibody include structures D-G in FIG. 6 and structures A, C and D of FIG. 7. Such structures are useful for nonreversibly attaching a targeting agent-linker to a reactive nucleophilic group (e.g. lysine or cysteine side chain) in the combining site of an antibody.

It should be understood that the above described reversible and nonreversible covalent linking chemistry can also be applied to link a targeting agent or biological agent to an antibody in the absence of a linker or to link a targeting agent or biological agent to a linker (e.g. to the connecting chain of the linker). For example, a targeting agent can be linked to a linker to form a targeting agent-linker by placing a suitable reactive group Z type element such as an appropriate nucleophilic or electrophilic group on either the linker or the targeting agent and a suitable reactive moiety such as an amino or sulfhydral group on the other of the two.

A preferred linker for use in targeting compounds of the invention and for preparing targeting agent-linker compounds includes a 1,3-diketone reactive group as Z. Another preferred linker is one where the connecting chain X includes a repeating ether unit of between 2-100 units. Linkers in which the recognition group Y is present are preferred with Y located preferably between 1-20 atoms from the reactive group Z. Such a linker attached to the core of an integrin targeting RGD peptidomimetic moiety such as those described above, can have the structure 28 as shown below where n is from 1-100 or more and preferably is 1, 2, or 4, and more preferably is 3. In some embodiments, the linker is a repeating polymer such as polyethylene glycol.

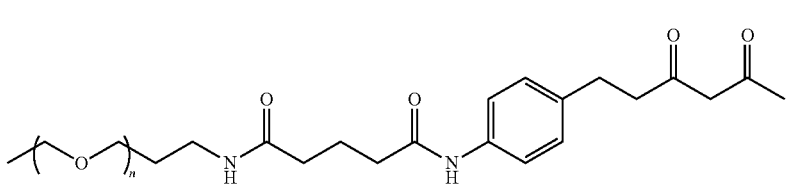

35

The linker reactive group or similar such reactive group that may be inherent in the targeting agent, is chosen for use with a particular antibody. For example, a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, eneamine, phosphate, phosphonate, epoxide, aziridine, thioepoxide, masked or protected diketone (ketal for example), lactam, haloketone, aldehyde, and the like. A 1,3-diketone configuration such as the diketone shown in Compound SCS-873 (see below) or SCS-864 (see below), is especially preferred as a substrate for modification by an aldolase antibody.

SCS873

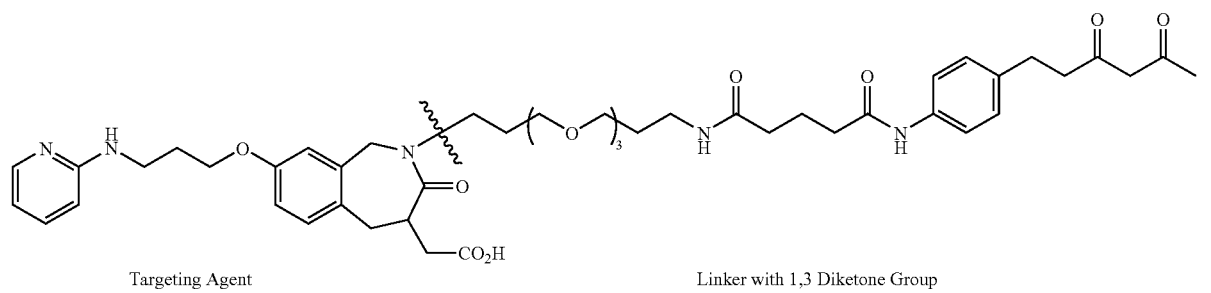

Targeting Agent           Linker with 1,3 Diketone Group

SCS864

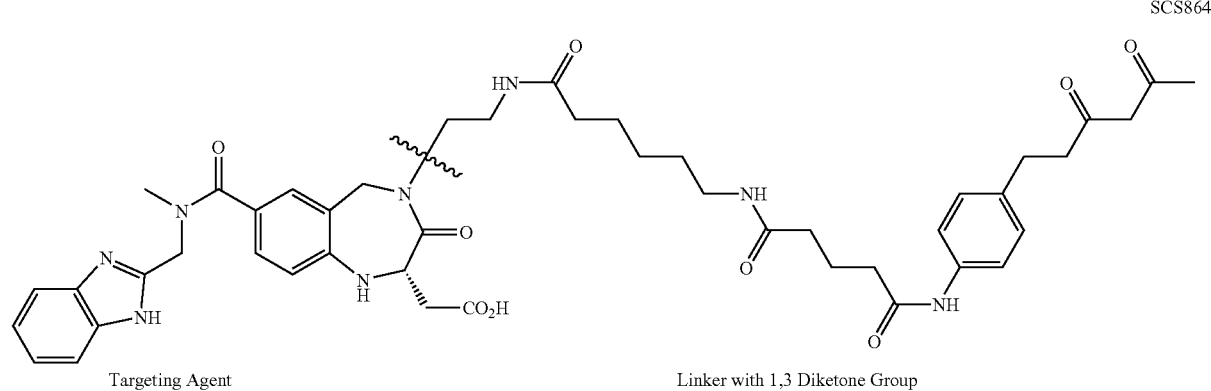

Targeting Agent           Linker with 1,3 Diketone Group

A linker reactive group chemical moiety (Z) suitable for covalent modification by a reactive sulfhydryl group in an antibody may be a disulfide, aryl halide, maleimide, alpha-haloacetamide, isocyanate, epoxide, thioester, active ester, amidine, guanidine, imine, eneamine, phosphate, phosphonate, epoxide, aziridine, thioepoxide, masked or protected diketone (ketal for example), lactam, haloketone, aldehyde, and the like. The chemical structures of various targeting agent-linker compounds which include a linker with a 1,3 diketone as the reactive group are shown in FIGS. 2-5.

One of skill in the art will readily appreciate that reactive amino acid side chains in antibodies may possess an electrophilic group that reacts with a nucleophilic group on the targeting agent or its linker, whereas in other embodiments a reactive nucleophilic group in an amino acid side chain of a combining site of an antibody or an antibody fragment reacts with an electrophilic group in a targeting agent or linker. Thus, antibody or antibody fragment combining site side chains may be substituted with an electrophile (e.g., FIGS. 6 and 7) and this group may be used to react with a nucleophile on the targeting agent or its linker (e.g., $NH_2$). In this embodiment, the antibody and targeting agent each have a partial linker with appropriate reactive moieties at each end so that the two ends of the partial linker can form the full linker, thus creating the complete targeting compound.

One of skill in the art also will readily appreciate that two or more targeting agents may be linked to a single antibody combining site. The two targeting agents may be the same or may be different with respect to their specificity for a particular target. In one embodiment, each targeting agent may be linked to a separate reactive side chain of an amino acid in the antibody combining site. In a preferred embodiment, the two targeting agents are attached to a branched or linear linker which then links both targeting agents to the same reactive amino acid side chain in the antibody combining site. Each branch of a branched linker may in some embodiments comprise a linear stretch of between 5-100 atoms. By way of example, the structures disclosed in FIGS. 3-5 show embodiments of branched linkers with two targeting agents linked to a different branch of the linker, which has a 1,3-diketone as the reactive group. As shown in these embodiments, the branch point may be in the connecting chain or in the recognition group (if present).

"Antibody" as used herein includes immunoglobulins which are the product of B cells and variants thereof as well as the T cell receptor (TcR) which is the product of T cells and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce $F(ab')_2$, a dimer of Fab which itself is a light chain joined to $V_H$-$CH_1$ by a disulfide bond. The $F(ab')_2$ may be reduced under mild conditions to break the disulfide linkage in the hinge region thereby converting the $F(ab')_2$ dimer into an Fab' monomer. The Fab' monomer is essentially a Fab fragment with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

The T cell receptor (TcR) is a disulfide linked heterodimer composed of α or β chains or, on a minority of T cells, γ or δ chains. The two chains are generally disulfide-bonded just outside the T cell plasma membrane in a short extended stretch of amino acids resembling the antibody hinge region. Each TcR chain is composed of one Antibody-like variable domain (Vα or Vβ) and one constant domain (Cα or Cβ). The full TcR has a molecular mass of about 95 kDa with the individual chains varying in size from 35 to 47 kDa. Also encompassed within the meaning of TCR are portions of the receptor such as the variable regions of this receptor that can be produced as a soluble protein using methods well known in the art. For example, U.S. Pat. No. 6,080,840 describes a soluble T cell receptor (TcR) prepared by splicing the extracellular domains of a TcR to the glycosyl phosphatidylinositol (GPI) membrane anchor sequences of Thy-1. The molecule is expressed in the absence of CD3 on the cell surface, and can be cleaved from the membrane by treatment with phosphatidylinositol specific phospholipase C (PI-PLC). The soluble TcR also may be prepared by coupling the TcR variable domains to an antibody heavy chain $CH_2$ or $CH_3$ domain, essentially as described in U.S. Pat. No. 5,216,132 or as soluble TcR single chains as described by Schusta et al. Nature Biotech. 18,754-759 (2000) or Holler et al. Proc. Natl. Acad. Sci (USA) 97:5387-5392 (2000). The TcR "antibodies" as soluble products may be used in place of antibody for making the compounds of the invention. The combining site of the TcR can be identified by reference to CDR regions and other framework residues using the same methods discussed above for antibodies.

Recombinant antibodies may be conventional full length antibodies, antibody fragments known from proteolytic digestion, unique antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker. See Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091, 513, 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. For example, antibody CDRs may be identified as the hypervariable regions originally defined by Kabat et al. (see, "Sequences of Proteins of Immunological Interest," E. Kabat et al., U.S. Department of Health and Human Services; Johnson, G and Wu, T T (2001) Kabat Database and its applications: future directions. Nucleic Acids Research, 29: 205-206; http://immuno.bme.nwa.edu). The positions of the CDRs may also be identified as the structural loop structures originally described by Chothia and others, (see Chothia and Lesk, J. Mol. Biol. 196, 901 (1987), Chothia et al., Nature 342, 877 (1989), and Tramontano et al., J. Mol. Biol. 215, 175 (1990)). Other methods include the "AbM definition" which is a compromise between Kabat and Chothia and is derived using Oxford Molecular's AbM antibody modeling software (now Accelrys) or the "contact definition" of CDRs by Macallum et al., ("Antibody-antigen interactions: contact analysis and binding site topography," J Mol Biol. Oct. 11, 1996; 262(5):732-45). The following chart identifies CDRs based upon various known definitions.

| Loop | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 (Kabat Numbering) | H31--H35B | H26--H35B | H26--H32..34 | H30--H35B |
| H1 (Chothia Numbering) | H31--H35 | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

General guidelines by which one may identify the CDRs in an antibody from sequence alone are as follows:

LCDR1:
Start-Approximately residue 24.
Residue before is always a Cys.
Residue after is always a Trp. Typically TRP is followed with TYR-GLN, but also may be followed by LEU-GLN, PHE-GLN, or TYR-LEU.
Length is 10 to 17 residues.

LCDR2:
Start-16 residues after the end of L1.
Sequence before is generally ILE-TYR, but also may be VAL-TYR, ILE-LYS, or ILE-PHE.
Length is generally 7 residues.

LCDR3:
Start-generally 33 residues after end of L2.
Residue before is a Cys.
Sequence after is PHE-GLY-X-GLY.
Length is 7 to 11 residues.

HCDR1:
Start-at approximately residue 26 (four residues after a CYS) [Chothia/AbM definition] Kabat definition starts 5 residues later.
Sequence before is CYS-X-X-X.
Residues after is a TRP, typically followed by VAL, but also followed by ILE, or ALA.
Length is 10 to 12 residues under AbM definition while Chothia definition excludes the last 4 residues.

HCDR2:
Start-15 residues after the end of Kabat/AbM definition of CDR-H1.
Sequence before typically LEU-GLU-TRP-ILE-GLY (SEQ ID NO. 1), but a number of variations are possible.
Sequence after is LYS/ARG-LEU/ILE/VAL/PHE/THR/ALA-THR/SER/ILE/ALA
Length is 16 to 19 residues under Kabat definition (AbM definition ends 7 residues earlier).

HCDR3:
Start-33 residues after end of CDR-H2 (two residues after a CYS).
Sequence before is CYS-X-X (typically CYS-ALA-ARG).
Sequence after is TRP-GLY-X-GLY.
Length is 3 to 25 residues.

The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al., (1988) Nature, 332:;323-327. The aldolase antibody mouse mAb 38C2, which has a reactive lysine near to but outside HCDR3, is an example of such an antibody.

The reactive residue of the antibody combining site may be naturally associated with the antibody such as when the residue is encoded by nucleic acid present in the lymphoid cell first identified to make the antibody. Alternatively, the amino acid residue may arise by purposely mutating so as to encode the particular residue (see, e.g., WO 01/22922 to Meares et al.). In another approach, the amino acid residue or its reactive elements (e.g., a nucleophilic amino group or sulfhydryl group) may be attached to an amino acid residue in the antibody combining site. Thus, covalent linkage with the antibody occurring "through an amino acid residue in the combining site of the antibody" as used herein means that linkage can be directly to an amino acid residue of an antibody combining site or through a chemical moiety that is linked to a side chain of an amino acid residue of an antibody combining site.

As discussed, antibodies that can be used in preparing the antibody targeting compounds of the invention require a reactive side chain in the antibody combining site. A reactive side chain may be present or be placed by mutation in any antibody. Catalytic antibodies are a preferred source of such antibodies. Such antibodies include aldolase antibodies, beta lactamase antibodies, esterase antibodies, amidase antibodies, and the like.

A reactive lysine in an antibody combining site may be covalently linked to a ketone, diketone, beta lactam, active ester haloketone, lactone, anhydride, maleimide, epoxide, aldehyde amidine, guanidine, imines, eneamines, phosphates, phosphonates, epoxides, aziridines, thioepoxides, masked or protected diketones (ketals for example), lactams, haloketones, aldehydes, and the like, associated with a targeting agent or linker-targeting agent. An exemplary and preferred such antibody is an aldolase antibody such as the mouse monoclonal antibody mAb 38C2 and other like catalytic antibodies as well as suitably humanized and chimeric versions of such antibodies. Mouse mAb 38C2 is the prototype of a new class of catalytic antibodies that were generated by reactive immunization and mechanistically mimic natural aldolase enzymes (Barbas et al., 1997, Science 278, 2085-2092). Through a reactive lysine, these antibodies catalyze aldol and retro-aldol reactions using the enamine mechanism of natural aldolases (Wagner et al., 1995, Science 270, 1797-1800; Barbas et al., 1997, Science 278, 2085-2092; Zhong et al., 1999, Angew. Chem. Int. Ed. 38, 3738-3741; Karlstrom et al., 2000, Proc. Natl. Acad. Sci. U.S.A., 973878-3883). In addition to their versatility and efficacy in synthetic organic chemistry (e.g., Hoffmann et al., 1998, J. Am. Chem. Soc. 120, 2768-2779; Sinha et al., 1998, Proc. Natl. Acad. Sci. U.S.A. 95, 14603-14608), aldolase antibodies have been used to activate camptothecin, doxorubicin, and etoposide prodrugs in vitro and in vivo as an anti-cancer strategy (Shabat et al., 1999, Proc. Natl. Acad. Sci. U.S.A. 96, 6925-6930 and ,2001, Proc. Natl. Acad. Sci. U.S.A. 98, 7528-7533).

In another example, the reactive amino acid of an antibody combining site may be a reactive cysteine, serine or tyrosine residue. For cysteines, the resulting antibody may form a covalent linkage with maleimide-containing components or other thiol-reactive groups such as iodoacetamides, aryl halides, disulfhydryls and the like. Reactive cysteines may be found in thioesterase catalytic antibodies as described by Janda et al., Proc. Natl. Acad. Sci. (USA) 91:2532-2536, (1994). For other esterase antibodies see Wirsching et al., Science 270:1775-82 (1995). Reactive amino acid-containing antibodies may be prepared by means well known in the art including mutating an antibody combining site residue to encode for the reactive amino acid or chemically derivatizing an amino acid side chain in an antibody combining site with a linker that contains the reactive group.

Antibodies suitable for use herein may be obtained by conventional immunization, reactive immunization in vivo, or by reactive selection in vitro, such as with phage display. Antibodies may be produced in humans or in other animal species. Antibodies from one species of animal may be modified to reflect another species of animal. For example, human chimeric antibodies are those in which at least one region of the antibody is from a human immunoglobulin. A human chimeric antibody is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. Chimeric and humanized antibodies may be prepared by methods well known in the art including CDR grafting approaches (see, e.g., U.S. Pat. Nos. 5,843,708; 6,180,370; 5,693,762; 5,585, 089; 5,530,101), chain shuffling strategies (see e.g., U.S. Pat. No. 5,565,332; Rader et al., Proc. Natl. Acad. Sci. USA (1998) 95:8910-8915), molecular modeling strategies (U.S. Pat. No. 5,639,641), and the like.

Unlike typical chemical derivatization of antibodies, those derived from reactive immunization can be specifically labeled in their binding site at a defined position, facilitating the rapid and controlled preparation of a homogeneous product. In addition, unlike chemical derivatization of antibodies, those derived from reactive immunization with 1,3-diketones are reversible. Due to this reversibility, a diketone derivative of a targeting compound bound to mAb 38C2 can be released from the antibody through competition with the covalent binding hapten J W (Wagner et al., 1995, Science 270, 1797-800), or related compounds. This allows one to immediately neutralize the conjugate in vivo in case of an adverse reaction. Alternatively, non-reversible covalent linkage is possible such as with aldolase antibodies and beta lactam derivatives of the targeting compound. Unlike typical anti-hapten antibodies, covalent diketone binding antibodies have the advantage that the covalent linkage that is formed between the diketone and antibody is stable to large changes in pH, either extremes of low pH 3 or high pH 11. Such pH shifts do not release the targeting compound from the antibody. This is an advantage for tumor targeting since tumors typically exhibit reduced pH as compared to normal tissues. The added stability of covalent binding antibodies covalently linked to their targeting agent should provide additional advantages in terms of formulation, delivery, and long term storage.

A targeting compound of the present invention can be made using techniques well known in the art. Typically, synthesis of a targeting agent which also is a functional component (biological agent) is the first step. The targeting agent (also functional component in this case) is then derivatized for linkage to a connecting component (the linker) which is then combined with the antibody. One of skill in the art will readily appreciate that the specific synthetic steps used depend upon the exact nature of the three components.

By way of example, as a first step, targeting agent-linker compounds shown as Compounds 15 and 4, was made as shown in Schemes 1 (FIG. 10) and 2 (FIG. 11), respectively, as derivatized versions of the integrin targeting agents shown as Compounds 1 and 2, above. Compounds 15 and 4 were derivatized (relative to Compounds 1 and 2) by addition of a portion of the linker (connecting component). Scheme 3 (FIG. 12) shows additional synthetic steps by which a complete linker with a diketone reactive moiety was added to derivatized targeting agent Compound 15 to obtain targeting compounds SCS-873 and SCS-1655.

Integrin targeting components shown as compounds 15 and 4 were synthesized as shown in the FIG. 10 (Scheme 1) and FIG. 11 (Scheme 2), respectively. A linker with a diketone reactive moiety was added to these targeting molecules as shown in Scheme 3 (FIG. 12) to form targeting compound-linker molecules SCS-873 and SCS-1655. Synthesis of SCS-873 was achieved starting from compound 14 in three steps. Compound 14 was converted to 15 as shown in Scheme 1 and the crude product was reacted with an N-hydroxysuccinimide (NHS)-ester of the diketone compound 23 in CH3CN-DMF in the presence of Et3N. Purification over silica gel (CH2Cl2-MeOH, 9:1) afforded pure SCS-873.

Compound SCS-1655 was synthesized from 14 in five steps (Schemes 2 and 3). Deprotection of the BOC group in compound 14 followed by reaction with the NHS ester of the bivalent linker 24 afforded compound 25, which was then deprotected and reacted with 23 as above to afford SCS-1655.

Synthesis of integrin targeting component-linker molecules SCS-864 and SCS-789 is shown in Scheme 4 (FIG. 13). SCS-864 and SCS-789 were each synthesized in one step from compound 4 (FIG. 13, scheme 4). Linking of Compound 4 was achieved with the appropriate activated NHS-ester.

Targeting agent-linker compounds, such as SCS-864, SCS-873 and SCS-1655 where the linker includes a diketone reactive moiety, can be incubated with 0.5 equiv. of an aldolase antibody such as mAb 38C2 to produce antibody targeting compounds. Additional examples are set forth below.

Also provided are targeting agent-linker compounds for covalently linking to a combining site of an antibody. The linker is of sufficient length to allow the targeting agent to bind to the target molecule when the targeting agent is linked through the linker to an antibody. In some embodiments, the targeting agent-linker compound includes one or more targeting agents specific for a target molecule with a linker of the formula X—Y—Z. The makeup of linker components X, Y and Z are as described above. If two or more targeting agents are included in the targeting agent-linker compound, the various targeting agents may be attached directly to the linker or the linker may be branched with targeting agents attached to different linker branches.

Also provided is a targeting agent-linker compound that can be noncovalently associated with the combining site of an antibody. This compound can be used in conjunction with a suitable antibody to form a targeting compound of the invention. Such targeting agent-linker compounds comprise two or more targeting agents covalently linked via a linker to an antigen recognized by the antibody. The linker may linear or branched and should be of sufficient length to allow the targeting agent(s) to bind to the target molecule when the targeting agent(s) is linked through the linker to the antibody.

In some embodiments, the linker includes any of C, H, N, O, P, S, Si, F, Cl, Br, and I, or a salt thereof. The linker also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. The linker also may include one or more ring structures. Combinations of the above groups and rings may also be present in the linkers of the targeting compounds of the invention. In some embodiments, the linker has a linear stretch of between 2-200 atoms although in other embodiments, longer linker lengths may be used. One or more targeting agents may be linked to the linker and if a branched linker is used, some of the targeting agents may be linked to different branches of the linker.

In some embodiments, the targeting agent of the targeting agent-linker compound is biologically active while in other embodiments, the targeting agent-linker compound further includes a separate biological agent, which is preferably covalently linked to the targeting agent. In some embodiments, the biological agent may be linked to the targeting agent or to the linker using essentially the same approaches used to link the targeting agent to the linker or using other approaches well known in the art.

The antigen of the linker can be any antigen which can be bound by an available antibody. Antigens are well known in the art and include, an organic compound, a drug, a biomolecule such as a protein, peptide, peptidomimetic, glycoprotein, proteoglycan, lipid, glycolipid, nucleic acid, carbohydrates, and the like as well as combinations of these molecules.

The present invention also includes methods of modifying the combining site of an antibody to generate binding specificity for a particular target molecule. Such methods include covalently linking a reactive amino acid side chain in the combining site of the antibody to a chemical moiety on a linker of a targeting agent-linker compound where the targeting agent is specific for the target molecule. The chemical moiety of the linker is sufficiently distanced from the targeting agent so that the targeting agent can bind to the target molecule when the targeting agent-linker compound is covalently linked to the antibody combining site. Typically, the antibody will not be considered specific for the target molecule. In a preferred embodiment, the antibody prior to covalent linking would have an affinity for the target molecule of less than about $1 \times 10^{-5}$ moles/liter. However, after the antibody is covalently linked to the targeting agent-linker compound, the modified antibody preferably has an affinity for the target molecule of at least about $1 \times 10^{-6}$ moles/liter, more preferably at least about $1 \times 10^{-7}$ moles/liter, even more preferably at least $1 \times 10^{-8}$ moles/liter, yet even more preferably at least $1 \times 10^{-9}$ moles/liter, most preferably at least about $1 \times 10^{-10}$ moles/liter.

The present invention also includes methods of altering at least one physical or biological characteristic of a targeting agent, biological agent or linker. The methods include covalently linking the targeting agent or biological agent to the combining site of an antibody as described above. In some embodiments, the targeting agent or biological agent is linked to the antibody combining site though a linker, the characteristics of which are described above. The method is particularly useful for linking small targeting or biological agents of 5 Kd or less. However, the method also works for larger such molecules. Characteristics of the targeting agent or biological agent can include binding affinity, susceptibility to degradation, such as by proteases, pharmocokinetics, pharmacodynamics, immunogenicity, solubility, solubility, lipophilicity, hydrophilicity, hydrophobicity, stability (more or less stable as well as planned degradation), rigidity, flexibility, modulation of antibody binding, and the like.

As used herein, pharmacokinetics refers to the concentration an administered compound in the serum over time. Pharmacodynamics refers to the concentration of an administered compound in target and nontarget tissues over time and the effects on the target tissue (efficacy) and the non-target tissue (toxicity). Improvements in, for example, pharmacokinetics or pharmacodynamics can be designed for a particular targeting agent or biological agent such as by using labile linkages or by modifying the chemical nature of any linker (changing solubility, charge, etc.).

The biological characteristic of an antibody targeting compound of the invention may be modified to obtain improved pharmaceutical or other characteristics. This may be achieved by altering one or more chemical characteristics of the targeting agent or biological agent, the linker or the antibody. A preferred approach is to chemically modify one or more chemical characteristics of the linker. By altering chemical characteristics of the compound including the linker, one can obtain improved features such as improvement in pharmockinetics, pharmacodynamics, solubility, immunogenicity and the like.

The targeting compounds of the present invention have many uses. For example, the antibody portion of a targeting compound may generally extend the half-life of a smaller sized targeting agent in vivo. Also, the biological potency of a particular targeting agent may be increased by the addition of effector function(s) provided by the antibody portion of the targeting compound (e.g., complement mediated effector functions). In addition, the targeting agent, through its increased size conferred by linkage to the antibody, may enable the targeting agent to function as a competitive inhibitor in situations where it would otherwise fail to do so. Thus, in one aspect, the invention provides a method for increasing the effective circulating half-life of a targeting agent. The method includes linking the targeting agent to an antibody using a linking group as set forth above. In another aspect, the invention provides a method of redirecting an antibody to a specific target. The method includes linking an antibody to a targeting agent through a linker as set forth above.

The invention also provides a method of treating or preventing a disease or condition in an individual wherein said disease or condition involves cells, tissue or fluid that expresses a target molecule. The method includes administering to a subject such as a patient, a therapeutically effective amount of a targeting compound of the invention. The subject may be an animal such as a mammal. In some embodiments, the subject is a human. The compound may include a biological agent that is the same or is distinct from the targeting agent and which may take any of the forms or activities described herein. In some preferred embodiments, the target molecule is an integrin and the disease is a carcinoma. The association of integrin expression in carcinomas is well known in the art (See, e.g., U.S. Pat. Nos. 5,753,230 and 5,766,591, the disclosures of which are incorporated herein by reference). For therapeutic use in humans, a human, humanized, or human chimeric antibody is a preferred as the antibody component of the targeting compound. An antibody with a human IgG4 constant region also is preferred if agonist activity is desired.

In addition to therapeutic applications, antibody targeting compounds of the invention may also be used for the imaging of cells such as tumor cells or tissues (e.g., an extracellular matrix biomolecule) as is well known in the art. Accordingly, provided is a method of imaging cells or tissue (e.g., an extracellular matrix biomolecule) in an individual. In such methods, the cells or tissue expresses a target molecule. The method includes administering to a subject an antibody targeting compound of the invention linked to a detectable label. A detectable label for use in such methods can be a radioisotope or may be a non-radioisotope such as may be used in nuclear magnetic resonance (NMR) imaging. In the latter case, one may link the antibody targeting agent to chelates e.g., diethylenetriaminepentaacetate (DTPA) of the paramagnetic metal gadolinium essentially as described in Simkins et al., Nat. Med., 4(5):623-6 (1998).

The binding of a mixture of SCS-873 and 38C2 to human Karposi's sarcoma SLK cells was studied. SCS-873 effectively mediated cell surface binding of 38C2. No binding of 38C2 was detectable in the absence of SCS-873. Control experiments confirmed that the 1,3-diketone moiety is required for binding of SCS-873 to 38C2. After independent i.p. and i.v. injections, respectively, SCS-873 and 38C2 form an integrin $\alpha_v\beta_3$ targeting conjugate in vivo. In these experiments, the circulatory half-life of SCS-873 was extended by more than two orders of magnitude through binding to 38C2. Combination of SCS-873 and 38C2 effectively inhibited tumor growth in a mouse model of human Karposi's sarcoma, whereas either SCS-873 or 38C2 alone were less effective or not effective at all.

The present invention also provides methods of targeting a biological activity to cells, tissue (e.g., an extracellular matrix biomolecule) or a biolomolecule in the fluid of a subject. The method includes administering to the subject, a targeting compound that includes a targeting agent specific for the cells, tissue extracellular matrix biomolecule or fluid biomolecule. The targeting agent is covalently linked to an amino acid residue in the combining site of an antibody. In some embodiments, a linker is used to link the targeting agent to the antibody. The targeting agent is not an antibody. In some embodiments, the compound has a biological activity while in other embodiments, an biologically active molecule that is not the targeting agent is included as a component of the compound. Alternatively, the component parts of the targeting compound may be separately administered and then form the covalent compound in vivo. In such a method, the targeting agent may include a linker/reactive moiety or the antibody combining site may be suitably modified to covalently link to the targeting agent.

A targeting compound of the present invention can be administered as a pharmaceutical or medicament that includes a targeting compound of the invention formulated with a pharmaceutically acceptable carrier. Accordingly, the compounds may be used in the manufacture of a medicament or pharmaceutical composition. Pharmaceutical compositions of the invention may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compounds may be combined with excipients such as cocoa butter, glycerin, gelatin or polyethylene glycols and molded into a suppository.

Compounds of the invention may be formulated to include other medically useful drugs or biological agents. The compounds also may be administered in conjunction with the administration of other drugs or biological agents useful for the disease or condition that the invention compounds are directed.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable. A compound can be administered parenterally, such as intravascularly, intravenously, intraarterially, intramuscularly, subcutaneously, or the like. Administration can also be orally, nasally, rectally, transdermally or inhalationally via an aerosol. The composition may be administered as a bolus, or slowly infused.

The administration of an antibody-targeting agent conjugate to an immunocompetent individual may result in the production of antibodies against the conjugate. Such antibodies may be directed to the antibody itself, such as the variable region including the antibody idiotype as well as to the targeting agent or any linker used to conjugate the targeting agent to the antibody. Reducing the immunogenicity of the antibody-targeting agent conjugate can be addressed by methods well known in the art such as by attaching long chain polyethylene glycol (PEG)-based spacers, and the like, to the antibody-targeting agent. Long chain PEG and other polymers are known for their ability to mask foreign epitopes, resulting in the reduced immunogenicity of therapeutic proteins that display foreign epitopes (Katre et al., 1990, *J. Immunol.* 144, 209-213; Francis et al., 1998, *Int. J. Hematol.* 68, 1-18). As noted, PEG can be a linker as well, thus providing both linker function and reduced immunogenicity in a targeting compound of the invention. Alternatively, or in addition, the individual administered the antibody-targeting agent conjugate may be administered an immunosuppressent such as cyclosporin A, anti-CD3 antibody, and the like.

A method of screening a chemical library for agonists or antagonists of a receptor is further provided. The method includes linking individual members of the chemical library to the combining site of an antibody and then testing the antibody linked library for binding to the receptor or for inhibition of binding between the receptor and a ligand for the receptor. By this approach, the present antibody targeting compounds provide a new format for high throughput screening to identify candidate small molecule chemicals such as drugs peptides peptidomimetics, organic compounds, and the like, that function for example, as antagonists or agonists. The relative small size of a useful candidate chemical molecule typically requires indirect screening such as in displacement or competition formats. As provided herein, one can build the chemical library on an antibody format, by linking individual drugs in the library to a combining site of an antibody.

Antibody combining site-tagged libraries may be prepared by synthesizing chemical candidates with a suitable linker comprising a particular linker moiety designed for covalent interaction with a particular antibody. Such linkers may include a diketone moiety to be used in conjunction with an aldolase antibody that includes a reactive lysine in the combining site. One skilled in the art would readily understand that other linkers and linker moieties (e.g., biotin) which have been described herein are clearly useful for this purpose.

Antibody combining site-tagged chemical libraries thus prepared can be used, for example, in receptor assays or cell bioassays where binding of each compound in the library may be monitored by detecting the linked antibody. Detection of the antibody portion of each compound may be accomplished by methods of antibody detection well known in the art. For example, the antibody may be linked to a detectable moiety such as an enzyme, fluorophore, radioisotope, and the like.

Indirect systems can also be used such as biotin-streptavidin. Libraries can be screened on cells or impure antigens such as viral lysates as well as on purified antigens. For example, libraries can be tested for binding or inhibition of binding using as the target, lysates run on protein gels, with the analysis focussed on a particular gel band. In the case where the receptor is expressed on a cell, binding or inhibition of binding can be determined by detecting cellular signaling events occurring (or not occurring as in the case of inhibition) downstream of said binding or inhibition of binding. Downstream cellular signaling can be detected with the aid of a reporter gene as is well known in the art (see, e.g., U.S. Pat. Nos. 5,618,720 and 5,670,113).

Screening of antibody tagged chemical libraries can be readily adapted for use with high throughput instruments. Screening may be done in vitro or in vivo. Furthermore, a biological display library such as a peptide phage library may be used to prepare an antibody combining site-tagged library. In such cases, the site of attachment of the linker moiety (e.g., diketone) can be the fusion point of the library to the biological carrier.

Also provided is an immunoassay method for determining the amount of analyte in a sample. Such methods include:
  (a) forming, in a medium containing a sample, a complex between the analyte and at least one antibody specific for the analyte;
  (b) analyzing the medium to detect the amount of the complex; and
  (c) relating the amount of the complex to the amount of analyte in the sample.

Such methods may also include forming the complex with at least one antibody that is specific for the analyte. The specificity of the antibody is provided by a non-antibody targeting agent specific for the analyte which is covalently linked to a reactive amino acid in the combining site of the antibody. Thus, the antibody targeting compounds of the invention can be used in immunoassays for detecting and measuring the amount of an analyte in a sample as has been done previously with conventionally prepared polyclonal or monoclonal antibodies. Such assays are well known in the art and include RIA, EIA, Western, ELISA, and the like. The assay formats may be competitive or non-competitive and may be direct or indirect. The antibody targeting compound can be used in the liquid phase and/or can be bound to a solid phase carrier. Carriers include glass, polystyrene, polypropylene, polyethylene, dextran, nylon, natural and modified cellulose, polyacrylamide, agarose, magnetite, and the like. The nature of the carrier can be either soluble or insoluble. The antibody targeting compound may be detectably labeled in any of various ways well known in the art. U.S. Pat. Nos. 4,659,678; 4,780,423; and 4,298,685 are exemplary of such assays.

Viewed in general terms, the amount of an analyte in a sample can be determined by forming, in a medium containing the sample, a complex between the analyte and at least one antibody specific for the analyte. The medium is then analyzed to determine the amount of the complex that is formed. Finally, the amount of complex formed is then related to the amount of analyte in the sample. As already described, this general approach can take many forms such as direct and indirect, homogenous or heterogeneous, and competitive and noncompetitive. In all cases, the antibody targeting compounds of the invention may be used to replace functions provided by conventionally prepared antibodies.

Also provided is a direct or indirect binding assay where the presence of an analyte is determined using an antibody specific for the analyte. In such methods, the presence of the analyte is determined using an antibody specific for the analyte. The antibody specificity results from a non-antibody targeting agent that is specific for the analyte, and the targeting agent is covalently linked to a reactive amino acid in the combining site of the antibody. Thus, antibody-targeting compounds of the invention can be used in qualitative assays in place of conventionally prepared antibodies.

It would be readily evident that the compounds of the invention find use not only in human medical therapy and diagnosis but also in veterinary, agricultural, environmental and other disciplines.

Also provided are methods of inhibiting or reducing the ability of a targeting agent or biological agent to cross a cell membrane. In these methods an antibody targeting compound is formed by covalently linking the combining site of an antibody that does not itself cross the cell membrane to the targeting agent or biological agent, wherein linkage of said antibody to said targeting agent or biological agent reduces or inhibits the ability of the agent to cross the cell membrane. Antibodies that are not directed to cell surface internalizing receptors are a preferred source of antibodies that do not cross cell membranes.

Further provided are methods of mediating intracellular delivery of a intracellularly active drug. In these methods, an antibody targeting compound is prepared wherein said compound includes one or more targeting agents or one or more biological agents or both covalently linked via a linker to the combining site of the antibody. The targeting agents or biological agents are characterized in that they bind to a cell receptor and mediate internalization of the agent. The antibody targeting compound also includes a drug that is active intracellularly. Intracellular drug delivery occurs when a cell expressing the receptor contacts the antibody targeting compound. The contacting results in internalization of the antibody targeting agent and delivery of said drug intracellularly.

This approach uses takes advantage of receptor mediated endocytosis (i.e., receptor mediated internalization) to deliver the antibody targeting compound intracellularly. Cell surface receptors that mediate internalization of binding ligands are well known in the art and include, for example, integrins, HER2, EGF receptor, folic acid receptor, and the like. Internalization assays are readily available and can be evaluated using fluorescent detection methods.

In some embodiments, the intracellularly active drug is a prodrug that becomes active when said drug contacts an intracellular compartment. The antibody targeting compound may include an intracellular trafficking signal to direct the internalized antibody targeting compound to a particular intracellular compartment. Many proteins contain one or more targeting sequences that serve as a trafficking signal or address to target the protein to the correct intracellular site. Receptors at the destination also may be involved in the trafficking process.

The sequences that direct proteins and other compounds to different intracellular sites such as endoplasmic reticulum, endosome, golgi, or nucleus, and the like, are well known in the art. For example, endoplasmic reticulum trafficking signals include a KDEL or KKXX sequence, golgi trafficking signals include a GRIP domain (see Munro et al., *Curr Biol* 9: 377-379, 1999), lysosomal trafficking signals (from golgi) include mannose-6-phosphate modified oligosaccharides, and nuclear localization trafficking signals which include one or two short positively charged sequences, e.g., lysine or arginine rich (see, Penco et al. Biotech Appl Biochem 34:151-159 2001).

The versatility of the invention is illustrated by the following Examples which illustrate preferred embodiments of the invention and are not limiting of the claims or specification in any way.

EXAMPLE 1

Antibody Targeting Compound Comprising an RGD Peptidomimetic Targeting Agent Covalently Linked to the Combining Site of Aldolase Monoclonal Antibody 38C2

An integrin targeting compound was formed based on the formation of a reversible covalent bond between a diketone linker derivative of an RGD peptidomimetic and the reactive lysine of mouse mAb 38C2. Mouse mAb 38C2 is the prototype for a new class of catalytic antibodies generated by reactive immunization and mechanistically mimic natural aldolase enzymes (Barbas et al., *Science* 278, 2085-2092, 1997). Through a reactive lysine, these antibodies catalyze aldol and retro-aldol reactions using the enamine mechanism of natural aldolases (Wagner et al., *Science* 270, 1797-1800, 1995; Barbas et al., *Science* 278, 2085-2092, 1997; Zhong et al., *Angew. Chem. Int. Ed.* 38, 3738-3741, 1999). In addition to their versatility and efficacy in synthetic organic chemistry, aldolase antibodies have been used in the activation of camptothecin, doxorubicin, and etoposide prodrugs in vitro and in vivo as an anti-cancer strategy (Shabat et al., *Proc. Natl. Acad. Sci. U.S.A.* 96, 6925-6930, 1999); Shabat, D. et al. *Proc. Natl. Acad. Sci. U.S.A.* 98, 7528-7533, 2001). Yet another feature of these antibodies, namely their ability to bind diketones covalently, has remained largely unexplored.

The RGD peptidomimetic used (see Compound 1) is specific for human integrin with a high binding affinity for $\alpha_v\beta_3$ at 0.9 nM and $\alpha_v\beta_5$ at 0.6 nM (specificity exhibited by minimal $a_{IIb}b_3$ binding) (Miller et al., supra). A diketone linker modified version of Compound 1, designated SCS-873, was prepared as described above.

A peptidomimetic RGD antagonist with known activity for both $\alpha_v\beta_3$ or $\alpha_v\beta_5$ binding is desirable because some of these compounds bind both murine and human integrins. Such species cross reactivity affords preclinical in vivo studies in animal angiogenesis models prior to human trials. In addition, the targeting compound may be used for the therapy of Kaposi's sarcoma which is associated with $\alpha_v\beta_3$ integrin.

SCS-873 was linked to antibody 38C2 by the following procedure: One milliliter antibody 38C2 in phosphate buffered saline (10 mg/ml) was added to 12 microliters of a 10 mg/mL stock solution of SCS-873 and the resulting mixture was maintained at room temperature for 2 hours prior to use.

The binding of a mixture of SCS-873 and 38C2 to SLK cells was evaluated. SCS-873 effectively mediated cell surface binding of 38C2. No binding of 38C2 was detectable in the absence of SCS-873. Control experiments confirmed that the diketone moiety of the linker is required for binding of SCS-873 to 38C2. It was determined that SCS-873 retains the integrin specificity of the integrin targeting component, i.e., no binding to $a_{IIb}b_3$ in ELISA was detected while binding to $\alpha_v\beta_3$ and $\alpha_v\beta_3$ was found to be strong. Independent i.p. and i.v. injections of the targeting compound prepared with SCS-873 and 38C2 versus each component alone into mice demonstrated integrin targeting in vivo. In these experiments, the serum half-life of SCS-873 was extended by more than two orders of magnitude through binding to 38C2. Free SCS-873 not bound to antibody had a serum half-life of only minutes while the combination of antibody and small molecule could be detected in the serum sampled from eye bleeds after several days.

EXAMPLE 2

Antibody Targeting Compound Comprising IL-4 as Targeting Agent Covalently Linked to the Combining Site of Aldolase Monoclonal Antibody 38C2

Kaposi's sarcoma tumor cells, among other human epithelial tumor cells, express interleukin-4 (IL-4) receptors that can be targeted with a recombinant chimeric protein consisting of IL-4 and a truncated form of bacterial toxin called Pseudomonas exotoxin (Husain et al., 1999, Nat. Med. 5, 817-822). Based on these studies, an IL-4 targeting compound for targeting mAb 38C2 to Kaposi's sarcoma tumor cells is prepared. A linker with a diketone reactive group is conjugated to a lysine side chain of IL-2 using a lysine reactive moiety such as N-hydroxysuccinimide (NHS). Alternatively, a recombinant IL-4 with an added free cysteine is used for conjugation to cysteine reactive moieties such as maleimide. To reduce immunogenicity associated with the linker portion of the targeting compound, the spacer (i.e. linker connecting chain) between the diketone reactive group on one end and the NHS or maleimide group on the other, is a polyethylene glycol (PEG) chain. Long chain PEG and other polymers are known for their ability to mask foreign epitopes, resulting in the reduced immunogenicity of therapeutic proteins that display foreign epitopes (Katre et al., 1990, J. Immunol. 144, 209-213; Francis et al., 1998, Int. J. Hematol. 68, 1-18). Not more than one to two diketones should be conjugated to the IL-4 in order to avoid clearance of cross-linked antibodies (Rehlaender and Cho, 1998, Pharm. Res. 15, 1652-1656). Other interleukins such as IL-2 can be used in place of IL-4 as the targeting agent. While IL-4 can be used primarily as a targeting module, an enhancement of its pharmacological effect (Lussow et al., 1996, Transplantation 62, 1703-1708) may result from IL-2 receptor triggering due to the prolonged serum half-life of the interleukin obtained through its linkage to an antibody.

EXAMPLE 3

Antibody Targeting Compound Comprising VEGF-R2 Binding Peptide as Targeting Agent Covalently Linked to the Combining Site of Aldolase Monoclonal Antibody 38C2

Vascular endothelial growth factor (VEGF) is a key modulator of tumor angiogenesis. Induced by hypoxia, VEGF expression is upregulated through the induction of VEGF mRNA transcription in the tumor. Following production and release by the tumor, VEGF diffuses to endothelial cells of nearby preexisting blood vessels, which display VEGF receptors (VEGFR). VEGF binds to two tyrosine kinase receptors, VEGFR-1 and VEGFR-2, which are expressed predominantly on endothelial cells. Activation of endothelial cells is associated with the binding of VEGF to VEGFR-2, whereas VEGFR-1 probably functions as a decoy receptor that regulates the local concentration of VEGF (Neufeld et al., 1999, FASEB J. 13, 9-22). Following activation, the endothelial cells proliferate, migrate directionally toward the tumor, and eventually roll up and interconnect to form new blood vessels. Anti-angiogenic drugs that interfere with the interaction of VEGF and VEGR-2 are promising candidates for cancer therapy (Klohs and Hamby, 1999, Curr. Opin. Biotechnol. 10, 544-549). Binétruy-Toumaire et al. (2000, EMBO J. 19, 1525-1533) identified the VEGFR-2 binding linear peptide ATWLPPR (SEQ ID NO: 2) through phage display of peptide libraries. ATWLPPR (SEQ ID NO: 2) effectively interfered with VEGF binding to VEGFR-2 and inhibited VEGF-mediated angiogenesis.

Figure 14:
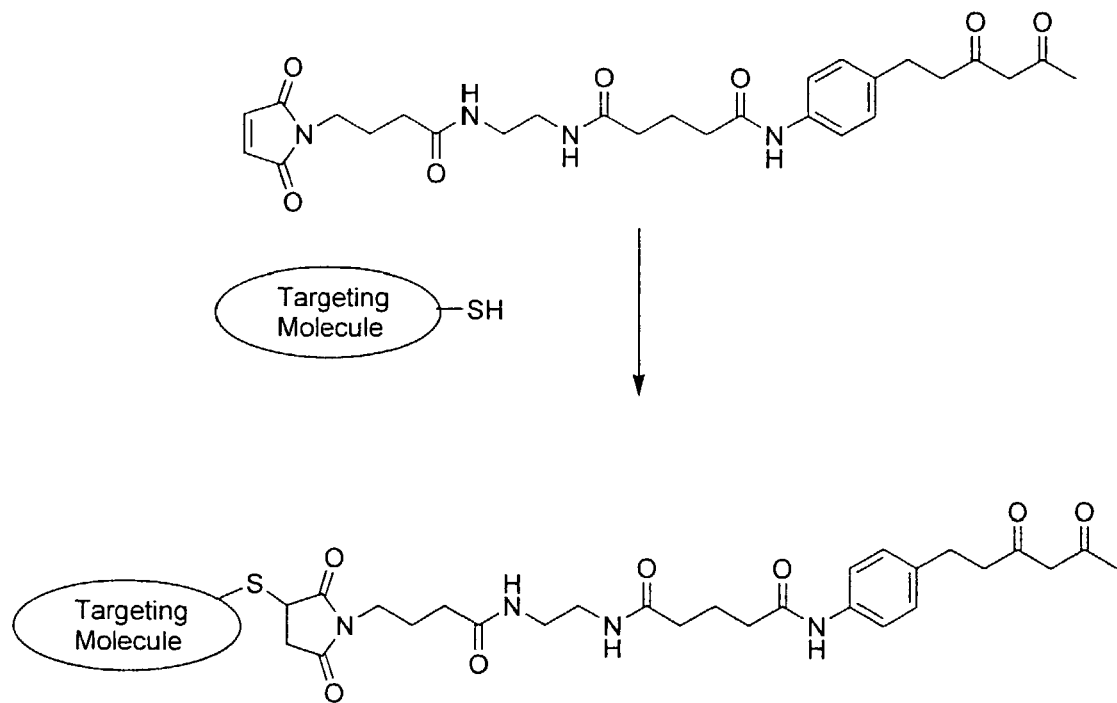
FIG. 14 shows a scheme for forming a targeting agent-linker compound using a linker with a maleimide-diketone reactive group.

An antibody targeting compound comprising VEGF-R2 binding peptide is prepared by synthesizing the peptide with an additional Cys residue at the amino or carboxy terminus, resulting in a peptide with the sequence ATWLPPRC (SEQ ID NO: 3) and CATWLPPR (SEQ ID NO: 4), respectively. These thiol-modified peptides are reacted with a maleimide/diketone linker (FIG. 14) to produce peptide-linker-diketo and diketo-linker-peptide. Incubation of these diketone derivatives with mAb38C2 results in a covalent linkage between the VEGFR-2 peptide and the antibody combining site. The resulting antibody-VEGFR-2 targeting compound is used to target endothelial cells that express VEGFR-2 such as in tumor angiogenesis. The compound prolongs the half-life of the peptide and equips it with antibody effector function.

EXAMPLE 4

Antibody Targeting Compound Comprising Neutralizing RNA Aptamer as Targeting Agent Covalently Linked to the Combining Site of Aldolase Monoclonal Antibody 38C2

Using the process of SELEX (Systematic Evolution of Ligands by Exponential Enrichment), RNA and DNA aptamers to a variety of molecular targets have been generated (Jayasena, 1999, Clin. Chem. 45, 1628-1650). For example, 2' fluoropyrimidine RNA aptamers that include about 25 nucleotides and that bind VEGF with an affinity in the 100-pM range were described (Ruckman et al., 1999, J. Biol. Chem. 32, 20556-20567). Like the peptide described in the previous example, the aptamers were found to interfere with the interaction of VEGF and VEGFR-2.

An antibody targeting compound comprising VEGF RNA aptamer is prepared using commercially available thiol-derivatized nucleotides such as 5'-phosphorothioate. A phosphorothioate group is a modified phosphate group with one of the oxygen atoms replaced by a sulfur atom. The thiol-modified nucleotide within the RNA aptamer is reacted with a maleimide diketone (e.g., FIG. 14) to produce an RNA aptamer targeting-diketone linker compound. Alternatively, a primary amino group is introduced into the RNA aptamer using commercially available amino modifiers. A nucleotide labeled with a primary amino group within the RNA aptamer is reacted with a linker that has N-hydroxysuccinimide diketone as the reactive group. Incubation of the diketone derivatives with mAb38C2 results in a covalent linkage between the RNA aptamer and the antibody combining site. The resulting antibody—RNA aptamer VEGFR-2 targeting compound is used to target endothelial cells that express VEGFR-2 such as in tumor angiogenesis. The compound prolongs the half-life of the RNA aptamer and equips it with antibody effector function.

EXAMPLE 5

Antibody Targeting Compound Comprising Folate as Targeting Agent Covalently Linked to the Combining Site of Aldolase Monoclonal Antibody 38C2

The folate receptor mediates the uptake of folic acid into cells by endocytosis. It is overexpressed on a variety of epithelial tumor cells (Leamon and Low, 2001, *Drug Discov. Today* 6, 44-51). For example, greater than 90% of ovarian carcinomas express the folate receptor (Sudimack and Lee, 2000, *Adv. Drug Deliv. Rev.* 41, 147-162). Mabs directed to the folate receptor, for example Mov18 and Mov19, have been evaluated as drugs for ovarian cancer therapy (Coney et al., 1994, *Cancer Res.* 54, 2448-2455; Molthoff et al., 1997, *Cancer* 80, 2712-2720). Folate-mediated targeting of cancer cells over expressing the folate receptor is an alternative strategy (Leamon and Low, 2001, *Drug Discov. Today* 6, 44-51). For example, chemotherapeutic drugs such as maytansinoids (Ladino et al., 1997, *Int. J. Cancer* 73, 859-864), are conjugated to folate for selective chemotherapy.

A targeting agent-linker compound comprising folate derivatized with a diketone shown in FIG. 2E is linked to mAb 38C2 and is used to target ovarian cancer cells. Because a majority of ovarian tumor cells also express integrins $\alpha_v\beta_3$ and/or $\alpha_v\beta_5$, in addition to the folate receptor, a dual targeting compound may be used for treatment. A targeting agent-linker compound comprising folate and an RGD peptidomimetic antagonist are together derivatized with a single diketone linker to form the dual targeting compound shown in FIG. 4B. The targeting agent-linker is linked to mAb 38C2 and is used to target ovarian cancer cells.

EXAMPLE 6

Antibody Targeting Compound Comprising an Inhibitor of Prostatic Acid Phosphatase or Prostate-Specific Antigen as Targeting Agent Covalently Linked to the Combining Site of Aldolase Monoclonal Antibody 38C2

Prostatic acid phosphatase (PAP) and prostate-specific antigen (PSA), a serine protease, are expressed on the cell surface of prostate tumor cells and are used as markers for prostate cancer. Mabs directed to PAP and PSA have long been considered promising drugs for prostate cancer therapy (Chang et al., 1999, *Curr. Opin. Urol.* 9, 391-395). More recently, small synthetic molecules that are specific inhibitors of PAP (Beers et al., 1996, *Bioorg. Med. Chem.* 4, 1693-1701) and PSA (Adlington et al., 2001, *J. Med. Chem.* 44, 1491-1508) have been reported. Other cell surface enzymes specific for prostate tumor cells, such as the recently identified serine protease hepsin (Magee et al., 2001, *Cancer Res.* 61, 5692-5696), also can be used as a target after specific small synthetic molecules or peptides targeting agents are identified.

A targeting agent-linker compound comprising a PAP and/or PSA inhibitor is derivatized with a diketone linker to form the compound shown in FIG. 2C. The targeting agent-linker is linked to mAb 38C2 and is used to target prostate cancer.

EXAMPLE 7

Antibody Targeting Compound Comprising Thrombopoietin Mimetic Peptides or Small-Molecule Agonists of the Thrombopoietin Receptor Covalently Linked to the Combining Site of Aldolase Monoclonal Antibody 38C2

The cell surface thrombopoietin receptor (cMp1, TPOR) is a member of the hematopoietic growth factor receptor superfamily. Thrombopoictin (TPO), the cytokine that binds to the thrombopoietin receptor, plays a central role in megakaryopoiesis and platelet production. Therapeutically, recombinant TPO is being tested in the clinic for the treatment of thrombocytopenia resulting from chemotherapy and bone marrow transplantation. As a therapeutic compound, TPO suffers from a relatively short half-life in vivo and from manufacturing and formulation short-comings.

A TPO targeting agent antibody compound is prepared to treat treatment of thrombocytopenia resulting from chemotherapy and bone marrow transplantation. The TPO mimetic peptide AF12505 with the sequence IEGPTLRQWLAARA (SEQ ID NO: 5), which has been reported to mimic the activity of recombinant TPO (Cwirla et al., 1997, *Science*, 276:1696-9), is synthesized with an additional Cys residue added to the amino terminus to produce CIEGPTLRQW-LAARA (SEQ ID NO: 6). This thiol-labeled peptide is then reacted with a maleimide/diketone linker (FIG. 14) to produce TPO peptide-linker (diketone) compound. Incubation of this diketone derivative with mAb38C2 generates an antibody-TPO receptor targeting compound.

In vitro assays are used to demonstrate that the targeted antibody binds live cells expressing the TPOR and stimulated megakaryocyte colony formation to a greater extent than the peptide AF12505. Other TPO mimetic peptides are known in the art and can also be used as the TPO receptor targeting agent. In addition, small-molecule mimetics with TPO receptor binding have recently been described by Kimura et. al (*FEBS Lett*, 1998, :428(3):250-4.) also may be used in preparing TPOR targeting compounds.

The above approach can be similarly applied to target the erythropoietin (EPO) receptor using EPO targeting mimetics that have increased therapeutic efficacy (Middleton et al., *J Biol Chem.*, 1999, 274(20):14163-9; Johnson et al., Nephrol Dial Transplant., 2000, 15(9):1274-7).

EXAMPLE 8

Antibody Targeting Compound Comprising T-20 Peptide or Small-Molecules that Bind the Envelope Proteins of HIV-1 Covalently Linked to the Combining Site of Aldolase Monoclonal Antibody 38C2

T-20, N-Acetyl-YTSLIHSLIEESQNQQEKNEQEL-LELDKWASLWNWF (SEQ ID NO: 7), a synthetic peptide corresponding to a region of the transmembrane subunit of the HIV-1 envelope protein, blocks cell fusion and viral entry at concentrations of less than 2 ng/ml in vitro. When administered intravenously, T-20 (monotherapy), the peptide decreases plasma HIV RNA levels demonstrating that viral entry can be successfully blocked in vivo. Administration of T-20 provides potent inhibition of HIV replication comparable to anti-retroviral regimens approved at present (Kilby et al., *Nat Med.*, 1998, 4(11):1302-7). This peptide drug suffers from a short half-life in vivo of approximately 2 hrs.

An antibody targeting compound using the T-20 peptide as targeting agent was produced to increase the valency, potency, and half-life of T-20. The T-20 peptide was synthesized with an additional Cys residue at the carboxy terminus, the resulting modified T-20 peptide having the sequence N-Acetyl-YTSLIHSLIEESQNQQEKNE QELLELDK-WASLWNWFC (SEQ ID NO: 8). This thiol-labeled peptide was then reacted with a maleimide/diketone linker (FIG. 14) to produce a T-20-Cys-linker compound. Incubation of this targeting agent-diketone linker with Ab38C2 resulted in a covalent linkage between the peptide and the antibody. In vitro assays demonstrated that the targeted antibody demonstrated increased potency in inhibiting HIV-1 entry and infection.

In addition to peptides that target the envelope proteins of HIV-1, a number of small-molecules that bind the envelope proteins have been described. For example, the betulinic acid derivative IC9564 is a potent anti-human immunodeficiency virus (anti-HIV) compound that can inhibit both HIV primary isolates and laboratory-adapted strains. Evidence suggests that HIV-1 gp120 plays a key role in the anti-HIV-1 activity of IC9564 (Holz-Smith et al., *Antimicrob Agents Chemother.*, 2001, 45(1):60-6.) Preparing an antibody targeting compound in which IC9564 is the targeting agent is expected to have increased activity over IC9564 itself by increasing valency, half-life, and by directing immune killing of HIV-1 infected cells based on the constant region of the antibody chosen. Similarly, recent X-ray crystallographic determination of the HIV-1 envelope glycoprotein gp41 core structure opened up a new avenue to discover antiviral agents for chemotherapy of HIV-1 infection and AIDS. Compounds with the best fit for docking into the hydrophobic cavity within the gp41 core and with maximum possible interactions with the target site can also be improved by addition of a diketone arm and covalent linkage to an antibody. Several compounds of this class have been identified (Debnath et al., *J Med Chem.,* 1999, 42(17):3203-9).

EXAMPLE 9

Antibody Targeting Compound Formation In Vivo via Transgenic Expression of the Antibody and Administration of the Targeting Agent-Linker Derivative Within the scope of the methods of the present invention is in vivo formation of the targeting compounds of the invention. In one approach, mAb 38C2 is produced in vivo from an inducible transgene and a targeting agent-linker derivative (e.g. diketone linker) is administered. Using gene delivery vectors, such as adenoviruses, cDNAs encoding light and heavy chain or a single-chain fragment of mAb 38C2 can be introduced into a host organism to establish the antibody transgene. This approach allows increased flexibility in treatment. For example, a patient with a general risk of cancer chooses to receive the transgene prior to the actual detection of the disease. Once cancer is diagnosed, expression of the reactive antibody (e.g. mAb 38C2) is induced in the patient and a targeting agent—linker derivative (e.g. diketone linker), where the targeting agent is specifically designed for targeting and affecting the diagnosed cancer, is administered. Ideally, both transgene induction and drug administration are accomplished orally, thus avoiding hospitalization.

EXAMPLE 10

Antibody Targeting Compound Libraries with Improved Detectability

Screening of small molecule or peptide antagonist, agonists, or simple binding molecules is often hampered by the assay available for the detection of the binding event. Often, displacement or competition assays are required where the small molecule displaces or competes with the binding of another molecule to the target site. The assay must frequently be specifically designed for the specific target molecule. The direct detection of a small molecule binding to either a cell surface or a protein is often not possible.

This problem is addressed by preparing the library in the form of antibody targeting compounds. To this end, small molecule libraries are synthesized with an appended reactive group such as a diketone or a high affinity tag such as biotin. Incubation of the tagged molecule with the target allows simple and sensitive detection of the binding event, accomplished using an enzyme-linked or fluorophore labeled antibody (e.g. 38C2 for the diketone) or streptavidin (for biotin). These types of assays are readily adapted for high throughput screening of compound and peptide libraries. The advantage of this direct screening of tagged molecules is that the detection method is sensitive and standardized over the diversity of possible cell surface molecules and protein or other soluble protein targets. Once identified, the attachment site of the linker arm does not need to be designed since it pre-exists in the tagged molecule. Therefore direct addition of the covalent binding antibody provides the novel therapeutic agent. In cases where a biotin tag is used for detection, the biotin arm is readily exchanged for a diketone arm for direct addition of the covalent binding antibody providing the novel therapeutic agent. If the library is a biological display library such as a peptide phage library, the site of attachment of the diketone arm is at the point where the peptide library resides are joined to the phage coat protein.

EXAMPLE 11

Antibody Targeting Compound Comprising TAK-779 Small-Molecules that Bind the Envelope Proteins of HIV-1 Covalently Linked to the Combining Site of Aldolase Monoclonal Antibody 38C2

The β-chemokine receptor CCR5 is an attractive target for inhibition of macrophage-tropic (CCR5-using or R5) HIV-1 replication because individuals having a nonfunctional receptor (a homozygous 32-bp deletion in the CCR5 coding region) are apparently normal, but are resistant to infection with R5 HIV-1. TAK-779 is a low molecular weight (Mr 531.13) nonpeptide CCR5-antagonist (Baba et al., (1999, Proc. Natl. Acad. Sci. USA, 96, 5698-5703). A targeting agent-linker compound was prepared by derivatizing TAK-779 with a diketo linker to yield the compound shown in FIG. 2D. The diketo-TAK-779 compound was incubated with Mab 38C2 to generate an antibody CCR5 targeting compound (TAK-799 based). This compound displayed highly potent and selective inhibition of R5 HIV-1 replication and bound specifically to CCR5 expressing cells. The antibody CCR5 targeting compound also displayed increased valency, increased biological potency, and increased serum half-life over that of the TAK-799 itself.

Other CCR5 antagonists (Shiraishi, et al., 2000, *J. Med. Chem.,* 43, 2049-2063) can also be modified for reaction with covalent binding antibodies to produce targeting compounds of the invention. A wide variety of chemokine receptor antagonists may also be modified using this approach.

EXAMPLE 12

Antibody Targeting Compound Comprising LHRH Peptide Covalently Linked to the Combining Site of Aldolase Monoclonal Antibody 38C2

[D-Lys6] LH-RH antagonist Glp-His-Trp-Ser-Tyr-D-Lys-Leu_Arg-Pro-Gly-NH2 (SEQ ID NO: 9) (100 micromoles) was dissolved in 1 mL anhydrous DMF. One equivalent of NHS-diketone linker (compound 35) was added with stirring overnight. Solvent was evaporated in vacuo, and the product was purified by HPLC. The resulting [D-Lys6] LH-RH-diketone linker compound was used directly for coupling to antibody 38C2. The resulting covalently-modified antibody specifically bound the OV-1063 human epithelial ovarian cancer line known to express the LH-RH receptor.

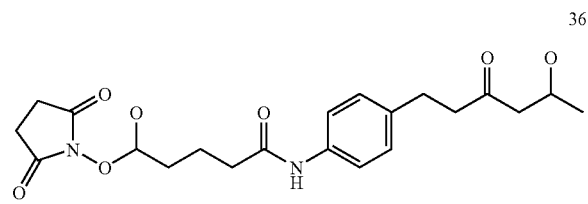

36

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure. All structures shown herein are contemplated to provide all enantiomers.

What is claimed is:

1. An antibody targeting compound comprising a therapeutic targeting agent at least 500 daltons in size covalently linked to the combining site of a catalytic antibody via a linker of the formula X—Y—Z, such that X is a linear or branched connecting chain of atoms comprising any of C, H, N, O, P, S, Si, F, Cl, Br, and I, or a salt thereof, and Y is an optional recognition group; and Z is a reactive group

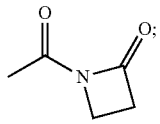

wherein the catalytic antibody is an aldolase antibody having a reactive lysine residue at its combining site;
wherein the targeting agent is linked to the X group of the linker; and whereby a side chain of the reactive lysine residue reacts with the beta lactam ring to form an amide linkage, and wherein the linkage forms an irreversible covalent bond.

2. The compound of claim 1 wherein antigen binding specificity of the antibody is substantially modified following the covalent linkage.

3. The compound of claim 1 wherein the combining site of said antibody is linked to the agent via a complementarity determining region.

4. The compound of claim 1 wherein said agent is linked to the combining site of said antibody via a variable framework region.

5. The compound of claim 1 wherein said antibody is full length.

6. The compound of claim 1 wherein said antibody is a fragment of a full length antibody.

7. The compound of claim 6 wherein said fragment of a full length antibody is Fab, Fab' F(ab')$_2$, Fv or sFv.

8. The compound of claim 1 wherein said antibody is a human antibody, humanized antibody or chimeric human antibody.

9. The compound of claim 1 wherein the X group of said linker comprises a linear stretch of between 5-100 atoms.

10. The compound of claim 1 wherein the X group of said linker comprises one or more groups selected from alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl group, phosphoalkyl, phosphoalkenyl, and phosphoalkynyl.

11. The compound of claim 1 wherein said linker comprises a repeating ether unit of between 2-100 units.

12. The compound of claim 1 wherein the compound further comprises a therapeutic drug covalently attached to the X group.

13. The compound of claim 12 wherein said therapeutic drug is a prodrug.

14. The compound of claim 1 wherein the targeting agent is specific for a biological molecule.

15. The antibody targeting compound of claim 14 wherein said biological molecule is a cell surface expressed or particle surface expressed ligand or receptor.

16. The antibody targeting compound of claim 15 wherein said cell surface expressed ligand or receptor is an integrin, a folate receptor, a cytokine receptor, an interleukin receptor, a viral protein or an enzyme.

17. The antibody targeting compound of claim 15 wherein said biological molecule is a fluid phase biomolecule.

18. The antibody targeting compound of claim 15 wherein said biological molecule is an extracellular matrix biomolecule.

19. A method of delivering a biological activity to cells, tissue extracellular matrix biomolecule or a biomolecule in the fluid of an individual, said method comprising administering to the individual the antibody targeting compound of claim 1 wherein said antibody targeting compound is specific for said cells, tissue extracellular matrix biomolecule or fluid biomolecule and wherein said antibody targeting compound comprises a biological activity.

20. A method of imaging cells or tissue in an individual wherein said cells or tissue expresses a target molecule, said method comprising administering to the individual the antibody targeting of claim 1 linked to a detectable label.

21. A method of reducing the infectivity of microbial cells or viral particles present on a surface, said method comprising contacting said surface with an effective amount of the antibody targeting compound of claim 1 wherein said antibody targeting compound comprises a therapeutic targeting agent specific for a receptor on said microbial cells or virus particles.

22. The compound of claim 1 wherein the Y-group has a formula that is either

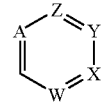

wherein A, Z, Y, X or W are independently C or N, or

wherein A, Z, Y or X are independently C, O, N or S.

23. The compound of claim 1 wherein the X-group of said linker is branched.

24. The compound of claim 23 wherein the branched ends of the X-group are attached to different molecules.

25. The compound of claim 23 wherein the branched ends of the X-group are attached to identical molecules.

26. The compound of claim 1 wherein the targeting agent comprises a peptide that is covalently linked to the X group of said linker.

27. The compound of claim 1 wherein the aldolase antibody is mouse monoclonal antibody 38C2 or humanized 38C2 antibody.

28. The compound of claim 22 wherein the Y-group comprises phenyl.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: antibody-heavy chain-complementarity
      determining regions-2; HCDR2

<400> SEQUENCE: 1

Leu Glu Trp Ile Gly
1               5

<210> SEQ ID NO 2
<211> LENGTH: 7
<212> TYPE: PRT
<213> ORGANISM: homo sapiens

<400> SEQUENCE: 2

Ala Thr Trp Leu Pro Pro Arg
1               5

<210> SEQ ID NO 3
<211> LENGTH: 8
<212> TYPE: PRT
<213> ORGANISM: Homo sapiens

<400> SEQUENCE: 3

Ala Thr Trp Leu Pro Pro Arg Cys
1               5

<210> SEQ ID NO 4
<211> LENGTH: 8
<212> TYPE: PRT
<213> ORGANISM: Homo Sapiens

<400> SEQUENCE: 4

Cys Ala Thr Trp Leu Pro Pro Arg
1               5

<210> SEQ ID NO 5
<211> LENGTH: 14
<212> TYPE: PRT
<213> ORGANISM: Homo Sapiens

<400> SEQUENCE: 5
```

Ile Glu Gly Pro Thr Leu Arg Gln Trp Leu Ala Ala Arg Ala
1               5                   10

<210> SEQ ID NO 6
<211> LENGTH: 15
<212> TYPE: PRT
<213> ORGANISM: Homo Sapiens

<400> SEQUENCE: 6

Cys Ile Glu Gly Pro Thr Leu Arg Gln Trp Leu Ala Ala Arg Ala
1               5                   10                  15

<210> SEQ ID NO 7
<211> LENGTH: 36
<212> TYPE: PRT
<213> ORGANISM: Artificial Sequence
<220> FEATURE:
<223> OTHER INFORMATION: A synthetic peptide corresponding to a region
      of the transmembrane subunit of the HIV-1 envelop protein, blocks
      cell fusion and viral entry at concentrations of less than
      2 ng/ml in vitro.
<220> FEATURE:
<221> NAME/KEY: ACETYLATION
<222> LOCATION: 1
<223> OTHER INFORMATION: N-acetyl tyrosine, the terminal
      amino group is acetylated

<400> SEQUENCE: 7

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 8
<211> LENGTH: 37
<212> TYPE: PRT
<213> ORGANISM: Artificial Sequence
<220> FEATURE:
<223> OTHER INFORMATION: A synthetic peptide corresponding to a region
      of the transmembrane subunit of the HIV-1 envelop protein, blocks
      cell fusion and viral entry at concentrations of less than
      2 ng/ml in vitro.  This one has a Cysteine at the C-terminus.
<220> FEATURE:
<221> NAME/KEY: ACETYLATION
<222> LOCATION: 1
<223> OTHER INFORMATION: N-acetyl tyrosine, the terminal amino group of
      this peptide has an acetyl group on it

<400> SEQUENCE: 8

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Cys
        35

<210> SEQ ID NO 9
<211> LENGTH: 10
<212> TYPE: PRT
<213> ORGANISM: Artificial Sequence
<220> FEATURE:
<223> OTHER INFORMATION: LH-RH antagonist
<220> FEATURE:
<221> NAME/KEY: MOD_RES
<222> LOCATION: 6
<223> OTHER INFORMATION: The lysine in this position is a D-lysine

```
<220> FEATURE:
<221> NAME/KEY: AMIDATION
<222> LOCATION: 10
<223> OTHER INFORMATION: The C-terminus is amidated with an amino group.
<220> FEATURE:
<221> NAME/KEY: MOD_RES
<222> LOCATION: 1
<223> OTHER INFORMATION: Xaa = pyroglutamic acid
    S-(-)-2-pyrrolidone-5-carbonyl residue,
    L-pyroglutamic acid residue

<400> SEQUENCE: 9

Xaa His Trp Ser Tyr Lys Leu Arg Pro Gly
1               5                   10
```